United States Patent
Ma et al.

(10) Patent No.: US 6,667,338 B2
(45) Date of Patent: Dec. 23, 2003

(54) 9-AMINO ERYTHROMYCIN DERIVATIVES WITH ANTIBACTERIAL ACTIVITY

(75) Inventors: Zhenkun Ma, Gurnee, IL (US); Ly Tam Phan, Malden, MA (US); Suoming Zhang, Brandford, CT (US); Stevan W. Djuric, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/050,837

(22) Filed: Jan. 16, 2002

(65) Prior Publication Data

US 2002/0142973 A1 Oct. 3, 2002

Related U.S. Application Data

(60) Provisional application No. 60/262,725, filed on Jan. 18, 2001.

(51) Int. Cl.$^7$ ............................................ A61K 31/335
(52) U.S. Cl. ........................ 514/450; 549/271; 549/272
(58) Field of Search ........................ 514/450; 549/271, 549/272

(56) References Cited

PUBLICATIONS

Dziegielewska, Irena et al, Erythromycin derivatives. Part X. Cyclic 11,12–carbonate of 9–amino–9–deoxoerythromycin A CA 93:47048 (1980).*

Asaka, Toshifumi et al, Preparation of erythromycin A derivatives as antibacterial agents 130:325342 (1999).*

* cited by examiner

Primary Examiner—Amelia Owens
(74) Attorney, Agent, or Firm—B. Coregory Donner

(57) ABSTRACT

Compounds of formula (I)

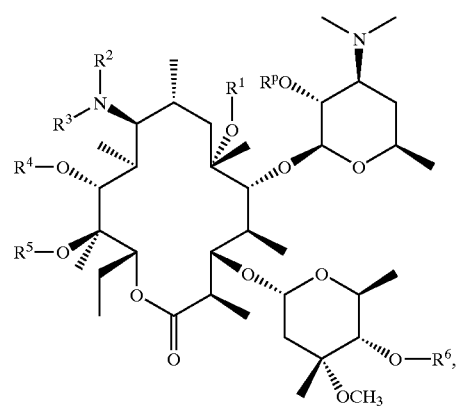

and formula (II)

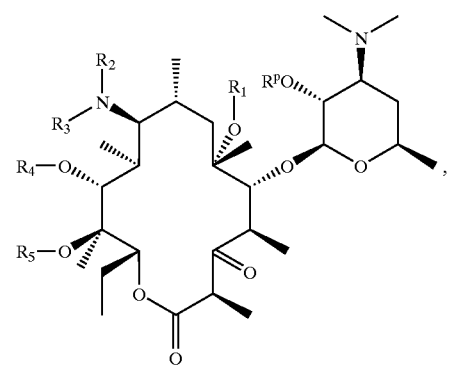

or therapeutically acceptable salts or prodrugs thereof are useful as antibacterial agents. Methods to make the compounds, compositions containing the compounds, and methods of treatment using the compounds are also disclosed.

21 Claims, No Drawings

9-AMINO ERYTHROMYCIN DERIVATIVES WITH ANTIBACTERIAL ACTIVITY

CROSS-REFERENCE TO RELATED APPLICATIONS

This application claims priority to U.S. Provisional Patent Application Serial No. 60/262,725, filed Jan. 18, 2001.

TECHNICAL FIELD

The present invention relates to 9-amino erythromycin derivatives which are antibacterial agents, compositions containing the compounds, methods for making the compounds, synthetic intermediates employed in the processes, and methods for the treatment of bacterial infections.

BACKGROUND OF THE INVENTION

Macrolide antibacterial agents are widely used to treat and prevent bacterial infections. However, the discovery of bacterial strains having resistance or insufficient susceptibility to macrolide antibacterial agents has spurred the development of compounds with modified or improved profiles of antibiotic activity. One such class of compounds are 9-amino erythromycin derivatives. 9-Amino erythromycin derivatives are macrolide antibacterial agents with a core ring structurally similar to the erythronolide A or B ring except for the presence of a substituted or unsubstituted nitrogen moiety at the 9-position. U.S. Pat. No. 6,025,350 discloses the preparation of C-4"-substituted 9-amino erythromycin derivatives. PCT application WO 99/21866, published May 6, 1999 discloses 9-aminoketolides.

The clinical application of macrolide antibiotics such as erythromycin is limited, due in part to their instability at lower pH, that is, low acid stability. Under acidic conditions, such as, for example, in the gut, intramolecular cyclization occurs as the 6-hydroxyl attacks the 9-keto group, leading to intermediates which lack significant antibacterial activity (J. Majer, *Antimicrob. Agents Chemother.*, 19, 628–633 (1981); K. Tsuji, *J. Chrom.*, 158, 337–348 (1978); G. S. Duthu, *J. Liq. Chrom.*, 7, 1023–1032 (1984)). The presence of the amino group at the 9-position would improve acid stability in this novel series of compounds.

Thus, novel 9-amino erythromycin derivatives which display improved profiles of antibacterial activity would represent a useful contribution to the art.

SUMMARY OF THE INVENTION

In its principle embodiment, therefore, the present invention provides 9-amino erythromycin derivatives of formula (I)

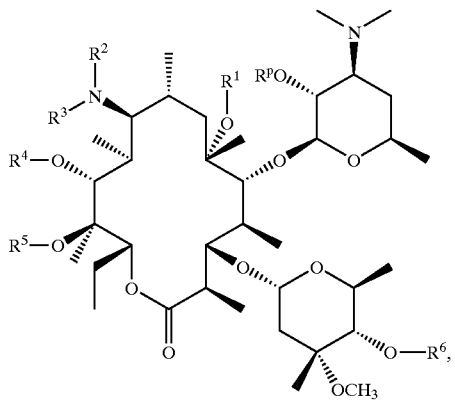

(I)

and formula (II)

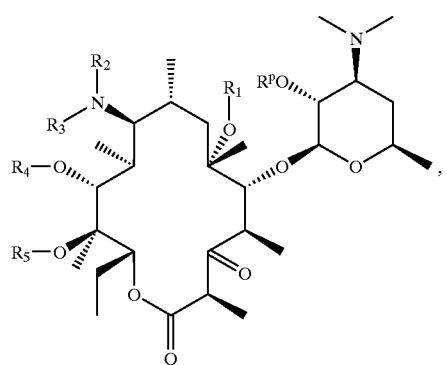

(II)

or therapeutically acceptable salts or prodrugs thereof, wherein $R^1$ is selected from hydrogen, alkyl, alkenyl, alkynyl, arylalkyl, arylalkenyl, arylalkynyl, (heterocycle)alkyl, (heterocycle)alkenyl, and (heterocycle)alkynyl, provided that $R^1$ is not hydrogen in compounds of formula (II);

$R^2$ and $R^3$ are independently selected from hydrogen, alkyl, alkenyl, alkynyl, alkanoyl, alkoxy, alkoxycarbonyl, alkylsulfonyl, arylalkyl, arylalkenyl, arylalkynyl, cycloalkyl, cycloalkylalkyl, cycloalkyloxycarbonyl, cycloalkyloyl, cycloalkylsulfonyl, cycloalkylaminocarbonyl, cycloalkylthiocarbonyl, aryl, arylalkyl, aroyl, aryloxycarbonyl, arylsulfonyl, alkylaminocarbonyl, alkylthiocarbonyl, arylaminocarbonyl, arylthiocarbonyl, heterocycle, (heterocycle)alkyl, (heterocycle)alkenyl, (heterocycle)alkynyl, (heterocycle)carbonyl, (heterocycle)aminocarbonyl, (heterocycle)oxycarbonyl, (heterocycle)thiocarbonyl, (heterocycle)sulfonyl, hydroxyl, and a nitrogen protecting group; or $R^1$ and $R^2$ together are selected from —C(O)—, —CH$_2$CH=CHCH$_2$—, alkylene, —CH$_2$C(O)—, and —C(O)CH$_2$—, wherein for —CH$_2$C(O)— and —C(O)CH$_2$—, each group is drawn with its left end attached to the nitrogen and its right end attached to the oxygen; or $R^2$ and $R^3$ taken together with the nitrogen atom to which they are attached form a heterocycle;

$R^4$ and $R^5$ are hydrogen; or $R^3$ and $R^4$ together are selected from —C(O)—, —CH$_2$CH=CHCH$_2$—, alkylene, —CH(R$^7$)—, —(CH$_2$)$_m$C(O)—, and —C(O)(CH$_2$)$_m$—, wherein m is an integer ranging from 1 to 4, and wherein for —(CH$_2$)$_m$C(O)— and —C(O)(CH$_2$)$_m$—, each group is drawn with its left end attached to the nitrogen and its right end attached to the oxygen; or $R^4$ and $R^5$ together are selected from —CH(R$^7$)— and —C(O)—;

$R^6$ is selected from hydrogen, alkanoyl, alkyl, aryl, carboxamido, and (heterocycle)carbonyl;

$R^7$ is selected from hydrogen, alkyl, alkenyl, aryl, arylalkyl, (heterocycle)alkyl and cycloalkyl; and $R^p$ is selected from hydrogen, trimethylsilyl, arylalkyl, aroyl, and alkanoyl.

In another embodiment, the present invention provides pharmaceutical compositions which comprise a therapeutically effective amount of a compound of formula (I) or a compound of formula (II), or therapeutically acceptable salts or prodrugs thereof, in combination with a therapeutically acceptable carrier.

In yet another embodiment, the present invention provides a method of treating bacterial infections in a host mammal in recognized need of such treatment comprising administering a therapeutically effective amount of a compound of formula (I) or a compound of formula (II), or therapeutically acceptable salts or prodrugs thereof.

In still yet another embodiment of the present invention are provided methods for the preparation of compounds of formula (I) and compounds of formula (II).

DETAILED DESCRIPTION OF THE INVENTION

It is understood that the following detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, and/or methods of use of the invention, may be made without departing from the spirit and scope thereof.

In one embodiment of the present invention are compounds having formula (I)

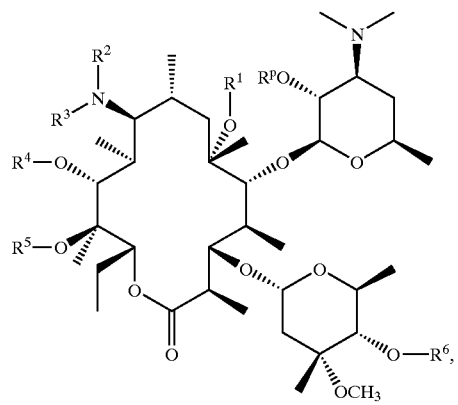

(I)

or therapeutically acceptable salts or prodrugs thereof, wherein $R^1$ is selected from hydrogen, alkyl, alkenyl, alkynyl, arylalkyl, arylalkenyl, arylalkynyl, (heterocycle)alkyl, (heterocycle)alkenyl, and (heterocycle)alkynyl;

$R^2$ and $R^3$ are independently selected from hydrogen, alkyl, alkenyl, alkynyl, alkanoyl, alkoxy, alkoxycarbonyl, alkylsulfonyl, arylalkyl, arylalkenyl, arylalkynyl, cycloalkyl, cycloalkylalkyl, cycloalkyloxycarbonyl, cycloalkyloyl, cycloalkylsulfonyl, cycloalkylaminocarbonyl, cycloalkylthiocarbonyl, aryl, arylalkyl, aroyl, aryloxycarbonyl, arylsulfonyl, alkylaminocarbonyl, alkylthiocarbonyl, arylaminocarbonyl, arylthiocarbonyl, heterocycle, (heterocycle)alkyl, (heterocycle)alkenyl, (heterocycle)alkynyl, (heterocycle)carbonyl, (heterocycle)aminocarbonyl, (heterocycle)oxycarbonyl, (heterocycle)thiocarbonyl, (heterocycle)sulfonyl, hydroxyl, and a nitrogen protecting group; or $R^1$ and $R^2$ together are selected from —C(O)—, —CH$_2$CH=CHCH$_2$—, alkylene, —CH$_2$C(O)—, and —C(O)CH$_2$—, wherein for —CH$_2$C(O)— and —C(O) CH$_2$—, each group is drawn with its left end attached to the nitrogen and its right end attached to the oxygen; or $R^2$ and $R^3$ taken together with the nitrogen atom to which they are attached form a heterocycle;

$R^4$ and $R^5$ are hydrogen; or $R^3$ and $R^4$ together are selected from —C(O)—, —CH$_2$CH=CHCH$_2$—, alkylene, —CH(R$^7$)—, —(CH$_2$)$_m$C(O)—, and —C(O)(CH$_2$)$_m$—, wherein m is an integer ranging from 1 to 4, and wherein for —(CH$_2$)$_m$C(O)— and —C(O)(CH$_2$)$_m$—, each group is drawn with its left end attached to the nitrogen and its right end attached to the oxygen; or $R^4$ and $R^5$ together are selected from —CH(R$^7$)— and —C(O)—;

$R^6$ is selected from hydrogen, alkanoyl, alkyl, aryl, carboxamido, and (heterocycle)carbonyl;

$R^7$ is selected from hydrogen, alkyl, alkenyl, aryl, arylalkyl, (heterocycle)alkyl and cycloalkyl; and $R^p$ is selected from hydrogen, trimethylsilyl, arylalkyl, aroyl, and alkanoyl.

The 9-amino group is the key feature of this molecular series, thus providing desirable physicochemical properties. Accordingly, the 9-amino group of the compounds of formula (I) can be unsubstituted or substituted in various ways, such substituents including, but not limited to, a nitrogen protecting group, alkanoyl, arylalkyl, (heterocycle)alkyl, alkyl, alkoxy, and the like.

In a preferred embodiment of the compounds of formula (I) of the present invention are compounds wherein $R^1$ is alkenyl, arylalkenyl, or (heterocycle)alkenyl. The alkenyl, arylalkenyl, (heterocycle)alkenyl groups can exist as geometric isomers which are distinguished by the disposition of substituents about the double bond. $R^2$, $R^3$, $R^4$, $R^5$, $R^6$, and $R^P$ are as defined in formula (I).

In another preferred embodiment of the compounds of formula (I) of the present invention are compounds wherein $R^2$ and $R^3$ are hydrogen; and $R^1$, $R^4$, $R^5$, $R^6$, and $R^P$ are as defined in formula (I).

In yet another preferred embodiment of the compounds of formula (I) of the present invention are compounds wherein $R^2$ is arylalkyl; and $R^1$, $R^3$, $R^4$, $R^5$, $R^6$, and $R^P$ are as defined in formula (I).

In still yet another preferred embodiment of the compounds of formula (I) of the present invention are compounds wherein $R^1$ and $R^2$ together are —C(O)—, thereby forming a cyclic carbamate; and $R^3$, $R^4$, $R^5$, $R^6$, and $R^P$ are as defined in formula (I).

In still yet another preferred embodiment of the compounds of formula (I) of the present invention are compounds wherein $R^4$ and $R^5$ together are —C(O)—, thereby forming a cyclic carbonate; and $R^1$, $R^2$, $R^3$, $R^6$, and $R^P$ are as defined in formula (I).

In another embodiment of the present invention are compounds having formula (II)

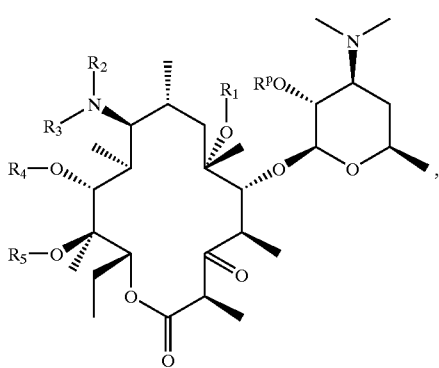

(II)

or therapeutically acceptable salts or prodrugs thereof, wherein $R^1$ is selected from alkyl, alkenyl, alkynyl, arylalkyl, arylalkenyl, arylalkynyl, (heterocycle)alkyl, (heterocycle)alkenyl, and (heterocycle)alkynyl;

$R^2$ and $R^3$ are independently selected from hydrogen, alkyl, alkenyl, alkynyl, alkanoyl, alkoxy, alkoxycarbonyl, alkylsulfonyl, arylalkyl, arylalkenyl, arylalkynyl, cycloalkyl, cycloalkylalkyl, cycloalkyloxycarbonyl, cycloalkyloyl, cycloalkylsulfonyl, cycloalkylaminocarbonyl, cycloalkylthiocarbonyl, aryl, arylalkyl, aroyl, aryloxycarbonyl, arylsulfonyl, alkylaminocarbonyl, alkylthiocarbonyl, arylaminocarbonyl, arylthiocarbonyl, heterocycle, (heterocycle)alkyl, (heterocycle)alkenyl, (heterocycle)alkynyl, (heterocycle)carbonyl, (heterocycle)aminocarbonyl, (heterocycle)oxycarbonyl, (heterocycle)thiocarbonyl, (heterocycle)sulfonyl, hydroxyl, and a nitrogen protecting group; or $R^1$ and $R^2$ together are selected from —C(O)—, —CH$_2$CH=CHCH$_2$—, alkylene, —CH$_2$C(O)—, and —C(O)CH$_2$—, wherein for —CH$_2$C(O)— and —C(O)CH$_2$—, each group is drawn with its left end attached to the nitrogen and its right end attached to the oxygen; or $R^2$ and $R^3$ taken together with the nitrogen atom to which they are attached form a heterocycle;

$R^4$ and $R^5$ are hydrogen; or $R^3$ and $R^4$ together are selected from —C(O)—, —CH$_2$CH=CHCH$_2$—, alkylene, —CH($R^7$)—, —(CH$_2$)$_m$C(O)—, and —C(O)(CH$_2$)$_m$—, wherein m is an integer ranging from 1 to 4, and wherein for —(CH$_2$)$_m$C(O)— and —C(O)(CH$_2$)$_m$—, each group is drawn with its left end attached to the nitrogen and its right end attached to the oxygen; or $R^4$ and $R^5$ together are selected from —CH($R^7$)— and —C(O)—;

$R^7$ is selected from hydrogen, alkyl, alkenyl, aryl, arylalkyl, (heterocycle)alkyl and cycloalkyl; and $R^P$ is selected from hydrogen, trimethylsilyl, arylalkyl, aroyl, and alkanoyl.

The 9-amino group is the key feature of this molecular series, thus providing desirable physicochemical properties. Accordingly, the 9-amino group of the compounds of formula (II) can be unsubstituted or substituted in various ways. $R^2$ therefore can vary considerably without departing from the intent of the invention.

In a preferred embodiment of the compounds of formula (II) of the present invention are compounds wherein $R^1$ is alkenyl, arylalkenyl, or (heterocycle)alkenyl. In a particularly preferred embodiment, $R^1$ is 3-$Y^1$-2-propenyl, wherein $Y^1$ is aryl or heterocycle. The alkenyl, arylalkenyl, (heterocycle)alkenyl groups can exist as geometric isomers which are distinguished by the disposition of substituents about the double bond. Accordingly, it will be appreciated by a skilled practitioner that compounds of formula (IIb)

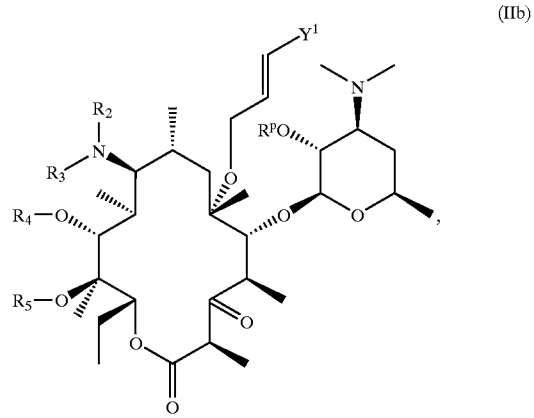

(IIb)

and therapeutically acceptable salts or prodrugs thereof, are contemplated as being within the scope of the present invention, wherein $R^2$, $R^3$, $R^4$, $R^5$, and $R^P$ are as defined in formula (II).

The compounds of formula (II) further comprise aryl or heterocyclic groups, represented by $Y^1$, connected to the parent molecular group through an alkenylene group. In a more preferred embodiment of the compounds of formula (II) of the present invention are compounds wherein $Y^1$ is a nitrogen-containing heterocycle which can be unsubstituted or substituted and moncyclic or bicyclic, such as, but not limited to pyridyl and quinolyl. Each of the aforementioned groups represented by $Y^1$ are connected to the alkenyl group through substitutable carbon atoms in the ring. $R^2$, $R^3$, $R^4$, $R^5$, and $R^P$ are as defined in formula (II).

In a particularly preferred embodiment of the compounds of formula (II) of the present invention are compounds wherein $Y^1$ is quinolin-3-yl. Accordingly, taking the list of preferred substituents and combinations thereof, it will be appreciated by a skilled practitioner that compounds of formula (IIc)

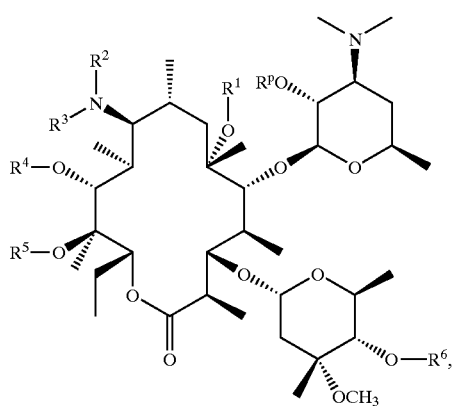

(I)

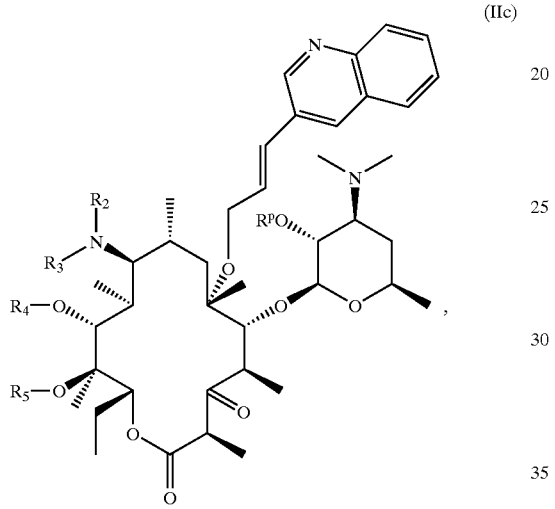

(IIc)

and formula (II)

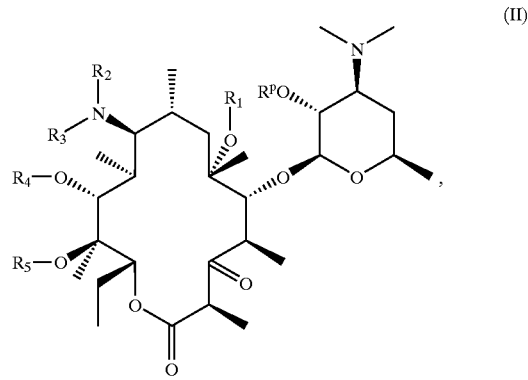

(II)

and therapeutically acceptable salts or prodrugs thereof, are contemplated as being within the scope of the present invention, wherein $R^2$, $R^3$, $R^4$, $R^5$, and $R^P$ are as defined in formula (II).

In another preferred embodiment of the compounds of formula (IIc) of the present invention are compounds wherein $R^2$ and $R^3$ are hydrogen, and $R^4$, $R^5$, and $R^P$ are as defined in formula (II).

In yet another preferred embodiment of the compounds of formula (IIc) of the present invention are compounds wherein $R^2$ is alkoxy; and $R^3$, $R^4$, $R^5$, and $R^P$ are as defined in formula (II).

In still yet another preferred embodiment of the compounds of formula (IIc) of the present invention are compounds wherein $R^3$ and $R^4$ together are —C(O)— or —CH$_2$—, thereby forming a cyclic carbamate and a heterocyclic ring, respectively; and $R^2$, $R^5$, and $R^P$ are as defined in formula (II).

In still yet another preferred embodiment of the compounds of formula (IIc) of the present invention are compounds wherein $R^4$ and $R^5$ together are —C(O)—, thereby forming a cyclic carbonate; and $R^2$, $R^3$, and $R^P$ are as defined in formula (II).

In another embodiment of the present invention is a method for the preparation of compounds of formula (I)

or therapeutically acceptable salts or prodrugs thereof, wherein
$R^1$ is selected from hydrogen, alkyl, alkenyl, alkynyl, arylalkyl, arylalkenyl, arylalkynyl, (heterocycle)alkyl, (heterocycle)alkenyl, and (heterocycle)alkynyl,
provided that $R^1$ is not hydrogen in compounds of formula (II);
$R^2$ and $R^3$ are independently selected from hydrogen, alkyl, alkenyl, alkynyl, alkanoyl, alkoxy, alkoxycarbonyl, alkylsulfonyl, arylalkyl, arylalkenyl, arylalkynyl, cycloalkyl, cycloalkylalkyl, cycloalkyloxycarbonyl, cycloalkyloyl, cycloalkylsulfonyl, cycloalkylaminocarbonyl, cycloalkylthiocarbonyl, aryl, arylalkyl, aroyl, aryloxycarbonyl, arylsulfonyl, alkylaminocarbonyl, alkylthiocarbonyl, arylaminocarbonyl, arylthiocarbonyl, heterocycle, (heterocycle)alkyl, (heterocycle)alkenyl, (heterocycle)alkynyl, (heterocycle)carbonyl, (heterocycle)aminocarbonyl, (heterocycle)oxycarbonyl, (heterocycle)thiocarbonyl, (heterocycle)sulfonyl, hydroxyl, and a nitrogen protecting group; or
$R^1$ and $R^2$ together are selected from —C(O)—, —CH$_2$CH=CHCH$_2$—, alkylene, —CH$_2$C(O)—, and —C(O)CH$_2$—, wherein for —CH$_2$C(O)— and —C(O)CH$_2$—, each group is drawn with its left end attached to the nitrogen and its right end attached to the oxygen; or
$R^2$ and $R^3$ taken together with the nitrogen atom to which they are attached form a heterocycle;

$R^4$ and $R^5$ are hydrogen; or $R^3$ and $R^4$ together are selected from —C(O)—, —CH$_2$CH=CHCH$_2$—, alkylene, —CH($R^7$)—, —(CH$_2$)$_m$C(O)—, and —C(O)(CH$_2$)$_m$—, wherein m is an integer ranging from 1 to 4, and wherein for —(CH$_2$)$_m$C(O)— and —C(O)(CH$_2$)$_m$—, each group is drawn with its left end attached to the nitrogen and its right end attached to the oxygen; or $R^4$ and $R^5$ together are selected from —CH($R^7$)— and —C(O)—;

$R^6$ is selected from hydrogen, alkanoyl, alkyl, aryl, carboxamido, and (heterocycle)carbonyl;

$R^7$ is selected from hydrogen, alkyl, alkenyl, aryl, arylalkyl, (heterocycle)alkyl and cycloalkyl; and $R^P$ is selected from hydrogen, trimethylsilyl, arylalkyl, aroyl, and alkanoyl, the method comprising:

(a) treating a compound of formula (Ia)

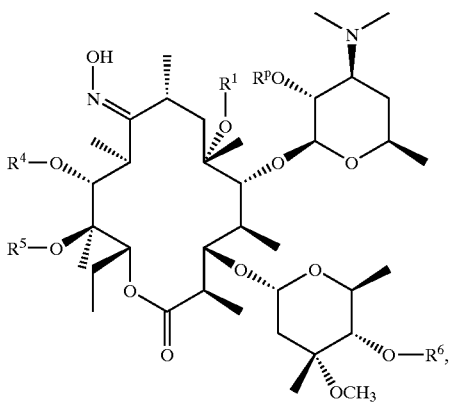

(Ia)

or a compound of formula (IIa)

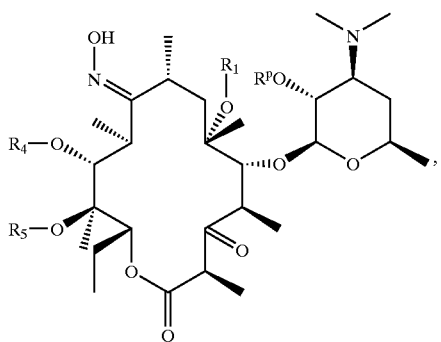

(IIa)

wherein, for compounds of formula (Ia) and (IIa), $R^1$, $R^4$, $R^5$, $R^6$, and $R^P$ are defined hereinabove, with a reducing agent in the presence of a first acid;

(b) optionally treating the product of step (a) with a second acid; and (c) optionally oxidizing and deprotecting the product of step (b).

DEFINITION OF TERMS

As used throughout this specification and the appended claims, the following terms have the meanings indicated:

The term "acid" or "buffering agent," as used herein, refers to reagents capable of donating protons during the course of a chemical reaction. Examples of acids include hydrochloric acid, acetic acid, trifluoroacetic acid, ammonium acetate, ammonium, chloride, ammonium nitrate, potassium hydrogensulfate, potassium hydrogenphosphate, potassium dihydrogenphosphate, sodium hydrogensulfate, sodium hydrogenphosphate, and sodium dihydrogenphosphate.

The term "additive" or "Lewis acid," as used herein, refers to reagents capable of accepting electrons during the course of a chemical reaction. Examples of Lewis acids include titanium(III) chloride, titanium(IV) chloride, molybdenum(VI) oxide, and nickel(II) chloride.

The term "alkanoyl," as used herein, refers to an alkyl group, connected to the parent molecular moiety through a carbonyl group.

The term "alkenyl," as used herein, refers to a straight or branched chain hydrocarbon containing from 3 to 12 carbons and containing at least one carbon-carbon double bond formed by the removal of two hydrogens. Representative examples of alkenyl include, but are not limited to, ethenyl, 1-propenyl, 2-propenyl, 2-methyl-2-propenyl, 2-butenyl, 3-butenyl, 4-pentenyl, and the like.

The term "alkenylene," as used herein, refers to a divalent group derived from a straight or branched chain hydrocarbon of 2 to 12 carbon atoms containing at least one double bond. Representative examples of alkenylene include, but are not limited to, vinylene, propenylene, butenylene, pentenylene, and the like.

The term "alkoxy," as used herein, refers to an alkyl group, connected to the parent molecular moiety through an oxygen atom.

The term "alkoxyalkyl," as used herein, refers to an alkoxy group, connected to the parent molecular moiety through an alkyl group.

The term "alkoxyalkoxy," as used herein, refers to an alkoxy group, connected to the parent molecular moiety through another alkoxy group.

The term "alkoxycarbonyl," as used herein, refers to an alkoxy group, connected to the parent molecular moiety through a carbonyl group.

The term "alkyl," as used herein, refers to a straight or branched chain hydrocarbon containing from 1 to 12 carbon atoms.

The term "alkylamino," as used herein, refers to an alkyl group, connected to the parent molecular moiety through an amino group.

The term "alkylaminocarbonyl," as used herein, refers to an alkylamino group, connected to the parent molecular moiety through a carbonyl group.

The term "alkylene," as used herein, refers to a divalent group derived from a straight or branched chain hydrocarbon of 1 to 12 carbon atoms.

The term "alkylsulfonyl," as used herein, refers to an alkyl group, connected to the parent molecular moiety through a sulfonyl group.

The term "alkylthio," as used herein, refers to an alkyl group, connected to the parent molecular moiety through a sulfur atom.

The term "alkylthiocarbonyl," as used herein, refers to an alkylthio group, connected to the parent molecular moiety through a carbonyl group.

The term "alkynyl," as used herein, refers to a straight or branched chain hydrocarbon group containing from 2 to 12 carbon atoms and containing at least one carbon-carbon triple bond.

The term "amino," as used herein, refers to —NH$_2$ or a derivative thereof formed by independent replacement of one or both hydrogen atoms thereon with a substituent or substituents independently selected from the group consisting of alkanoyl, alkenyl, alkyl, alkylsulfonyl, alkynyl, aminosulfonyl, aryl, arylalkenyl, arylalkyl, aroyl, arylsulfonyl, cycloalkyl, cycloalkylalkyl, cycloalkyloyl, cycloalkylsulfonyl, heterocycle, (heterocycle)alkyl, (heterocycle)carbonyl, (heterocycle)alkenyl, (heterocycle)sulfonyl, and a nitrogen protecting group.

The terms "amino protecting group," and "nitrogen protecting group," as used herein, refer to selectively introducible and removable groups, which protect amino groups against undesirable side reactions during synthetic procedures. Examples of amino protecting groups include trichloroethoxycarbonyl, benzyloxycarbonyl (Cbz), chloroacetyl, trifluoroacetyl, phenylacetyl, formyl, acetyl, benzoyl, tert-butoxycarbonyl (Boc), para-methoxybenzyloxycarbonyl, diphenylmethoxycarbonyl, phthaloyl, succinyl, benzyl, diphenylmethyl, triphenylmethyl (trityl), methanesulfonyl, para-toluenesulfonyl, trimethylsilyl, triethylsilyl, triphenylsilyl, and the like.

The term "aminoalkyl," as used herein, refers to an amino group, connected to the parent molecular moiety through an alkyl group.

The term "aminocarbonyl" or "carboxamido," as used herein, refers to an amino group, connected to the parent molecular moiety through a carbonyl group.

The term "aminosulfonyl," as used herein, refers to an amino group, connected to the parent molecular moiety through a sulfonyl group.

The term "aryl," as used herein, refers to a monocyclic carbocyclic ring system, or a bicyclic carbocyclic fused ring system wherein one or more of the fused rings are aromatic. The aryl group can be optionally fused to another aryl group, a cycloalkyl group, or a cycloalkenyl group. Aryl groups of the invention are exemplified by phenyl, naphthyl, indenyl, indanyl, dihydronaphthyl, tetrahydronaphthyl, and the like. The aryl groups are connected to the parent molecular group through a substitutable carbon. The aryl groups of the invention can be optionally substituted with 1–5 substituents independently selected from alkyl, alkenyl, alkynyl, alkylsulfonyl, alkoxyalkoxy, amino, aminoalkyl, aminosulfonyl, azido, cyano, cyanoalkyl, halo, haloalkyl, hydroxy, hydroxyalkyl, nitro, perfluoroalkyl, perfluoroalkoxy, oxo, —(CH$_2$)$_a$C(O)R$^8$, —(CH$_2$)$_a$OC(O)R$^8$, —(CH$_2$)$_a$C(O)OR$^8$, —(CH$_2$)$_a$N(R$^8$)C(O)R$^8$, —(CH$_2$)$_a$C(O)N(R$^8$)$_2$, —(CH$_2$)$_a$N(R$^8$)C(O)N(R$^8$)$_2$, —(CH$_2$)$_a$OR$^8$, —(CH$_2$)$_a$SO$_2$R$^8$, —(CH$_2$)$_a$SR$^8$, and —(CH$_2$)$_a$R$^9$; wherein a is zero to six;

R$^8$ is selected from hydrogen, unsubstituted or substituted alkyl, unsubstituted or substituted cycloalkyl, unsubstituted or substituted aryl, and unsubstituted or substituted heterocycle; and R$^9$ is selected from unsubstituted or substituted aryl, and unsubstituted or substituted heterocycle.

The term "arylalkenyl," as used herein, refers to an aryl group, connected to the parent molecular moiety through an alkenyl group.

The term "arylalkyl," as used herein, refers to an aryl group, connected to the parent molecular moiety through an alkyl group.

The term "arylalkynyl," as used herein, refers to an aryl group, connected to the parent molecular moiety through an alkynyl group.

The term "arylamino," as used herein, refers to an aryl group, connected to the parent molecular moiety through an amino group.

The term "arylaminocarbonyl," as used herein, refers to an arylamino group, connected to the parent molecular moiety through a carbonyl group.

The term "aryloxy," as used herein, refers to an aryl group, connected to the parent molecular moiety through an oxygen atom.

The term "aryloxycarbonyl," as used herein, refers to an aryloxy group, connected to the parent molecular moiety through a carbonyl group.

The term "aroyl," as used herein, refers to an aryl group, connected to the parent molecular moiety through a carbonyl group.

The term "arylsulfonyl," as used herein, refers to an aryl group, connected to the parent molecular moiety through a sulfonyl group.

The term "arylthio," as used herein, refers to an aryl group, connected to the parent molecular moiety through a sulfur atom.

The term "arylthiocarbonyl," as used herein, refers to an arylthio group, connected to the parent molecular moiety through an carbonyl group.

The term "azido," as used herein, refers to an —N$_3$ group.

The term "carbonyl," as used herein, refers to a —C(O)— group.

The term "carboxaldehyde" or "formyl," as used herein, refers to —CHO.

The terms "carboxyl" or "carboxy," as used herein, refers to —CO$_2$H or a derivative thereof formed by replacement of the hydrogen atom thereon with a carboxyl protecting group.

The terms "carboxy protecting group," and "carboxyl protecting group," as used herein refer to a carboxylic acid protecting ester group employed to block or protect the carboxylic acid functionality while the reactions involving other functional sites of the compound are carried out. In addition, a carboxy-protecting group can be used as a prodrug whereby the carboxy protecting group can be readily cleaved in vivo, for example by enzymatic hydrolysis, to release the biologically active parent. Representative carboxy-protecting groups are methyl, ethyl or tert-butyl; benzyl; 4-methoxybenzyl; nitrobenzyl; dimethylaminoethyl; pivaloyloxymethyl, propionyloxymethyl; benzoyloxyethyl; methoxycarbonylmethyl, cyclohexyloxycarbonylmethyl; tert-butyloxycarbonyloxymethyl; tert-butyloxycarbonylaminomethyl; methylaminocarbonylaminomethyl; acetylaminomethyl; 4-methylpiperazinylcarbonyloxymethyl; dimethylaminocarbonylmethyl; (5-tert-butyl-2-oxo-1,3-dioxolen-4-yl)methyl; (5-phenyl-2-oxo-1,3-dioxolen-4-yl)methyl, and the like.

The term "carboxyalkyl," as used herein, refers to a carboxyl group, connected to the parent molecular moiety through an alkyl group.

The term "cyano," as used herein, refers to a —CN group.

The term "cyanoalkyl," as used herein, refers to a cyano group, connected to the parent molecular moiety through an alkyl group.

The term "cycloalkyl," as used herein, refers to a saturated cyclic or bicyclic hydrocarbon group containing from 3 to 8 carbons.

The term "cycloalkylalkyl," as used herein, refers to cycloalkyl group, connected to the parent molecular moiety through an alkyl group.

The term "cycloalkoxy" or "cycloalkyloxy," as used herein, refers to cycloalkyl group, connected to the parent molecular moiety through an oxygen atom. The cycloalkyl part of the cycloalkoxy can be optionally substituted with one, two, or three groups independently selected from the group consisting of alkoxy, alkoxycarbonyl, alkyl, amino, hydroxyl, and oxo.

The term "cycloalkoxycarbonyl" or "cycloalkyloxycarbonyl," as used herein, refers to cycloalkoxy group, connected to the parent molecular moiety through a carbonyl group.

The term "cycloalkylamino," as used herein, refers to a cycloalkyl group, connected to the parent molecular moiety through an amino group.

The term "cycloalkylaminocarbonyl," as used herein, refers to a cycloalkylamino group, connected to the parent molecular moiety through a carbonyl group.

The term "cycloalkyloyl," as used herein, refers to cycloalkyl group, connected to the parent molecular moiety through a carbonyl group.

The term "cycloalkylsulfonyl," as used herein, refers to a cycloalkyl group, connected to the parent molecular moiety through a sulfonyl group.

The term "cycloalkylthio," as used herein, refers to a cycloalkyl group, connected to the parent molecular moiety through a sulfur atom.

The term "cycloalkylthiocarbonyl," as used herein, refers to a cycloalkylthio group, connected to the parent molecular moiety through a carbonyl group.

The terms "halo" or "halide," or "halogen," as used herein, refers to F, Cl, Br, or I.

The term "haloalkoxy," as used herein, refers to a halogen, connected to the parent molecular moiety through an alkoxy group.

The term "haloalkyl," as used herein, refers to a halogen, connected to the parent molecular moiety through an alkyl group.

The term "heterocycle" or "heterocyclic," as used herein, refers to a monocyclic, bicyclic, or tricyclic ring system. Monocyclic ring systems are exemplified by any 3- or 4-membered ring containing a heteroatom independently selected from oxygen, nitrogen and sulfur; or a 5-, 6- or 7-membered ring containing one, two or three heteroatoms wherein the heteroatoms are independently selected from nitrogen, oxygen and sulfur. The 5-membered ring has from 0–2 double bonds and the 6- and 7-membered ring have from 0–3 double bonds. Representative examples of monocyclic ring systems include, but are not limited to, azetidinyl, azepinyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinyl, pyranyl, pyrazinyl, pyrazolyl, pyrazolinyl, pyrazolidinyl, pyridyl, pyrimidinyl, pyridazinyl, pyrrolyl, pyrrolinyl, pyrrolidinyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above monocyclic ring systems fused to an aryl group, a cycloalkyl group, or another monocyclic ring system. Representative examples of bicyclic ring systems include but are not limited to, for example, benzimidazolyl, benzothiazolyl, benzothienyl, benzoxazolyl, benzofuranyl, benzopyranyl, benzothiopyranyl, benzodioxinyl, 1,3-benzodioxolyl, cinnolinyl, indazolyl, indolyl, indolinyl, indolizinyl, naphthyridinyl, isobenzofuranyl, isobenzothienyl, isoindolyl, isoindolinyl, isoquinolinyl, phthalazinyl, pyranopyridyl, quinolinyl, quinolizinyl, quinoxalinyl, quinazolinyl, tetrahydroisoquinolinyl, tetrahydroquinolinyl, and thiopyranopyridyl. The heterocyclic groups of this invention can be connected to the parent molecular moiety through a substitutable carbon atom or a substitutable nitrogen atom in the ring. The heterocycles of this invention can be optionally substituted with 1–5 substituents independently selected from alkyl, alkenyl, alkynyl, alkylsulfonyl, alkoxyalkoxy, amino, aminoalkyl, aminosulfonyl, azido, cyano, cyanoalkyl, halo, haloalkyl, hydroxy, hydroxyalkyl, nitro, perfluoroalkyl, perfluoroalkoxy, oxo, —$(CH_2)_aC(O)R^8$, —$(CH_2)_aOC(O)R^8$, —$(CH_2)_aC(O)OR^8$, —$(CH_2)_aN(R^8)C(O)R^8$, —$(CH_2)_aC(O)N(R^8)_2$, —$(CH_2)_aN(R^8)C(O)N(R^8)_2$, —$(CH_2)_aOR^8$, —$(CH_2)_aSO_2R^8$, —$(CH_2)_aSR^8$, and —$(CH_2)_aR^9$;

wherein a is zero to six;

$R^8$ is selected from hydrogen, unsubstituted or substituted alkyl, unsubstituted or substituted cycloalkyl, unsubstituted or substituted aryl, and unsubstituted or substituted heterocycle; and $R^9$ is selected from unsubstituted or substituted aryl, and unsubstituted or substituted heterocycle.

The term "(heterocycle)alkenyl," as used herein, refers to a heterocyclic group, connected to the parent molecular moiety through an alkenyl group. Representative examples of (heterocycle)alkenyl include, but are not limited to, 3-(2-pyridyl)-2-propenyl, 3-(3-pyridyl)-2-propenyl, 3-(4-pyridyl)-2-propenyl, 3-(2-quinolinyl)-2-propenyl, 3-(3-quinolinyl)-2-propenyl, and 3-(4-quinolinyl)-2-propenyl. The heterocycles of this invention can be optionally substituted with 1, 2, or 3 substituents independently selected from alkanoyl, alkenyl, alkoxy, alkoxyalkoxy, alkoxyalkyl, alkoxycarbonyl, alkyl, alkylsulfonyl, alkylthio, alkynyl, amino, aminoalkyl, aminocarbonyl, aminosulfonyl, carboxy, carboxyalkyl, cyano, cyanoalkyl, formyl, halogen, haloalkoxy, haloalkyl, hydroxy, hydroxyalkyl, mercapto, and nitro.

The term "(heterocycle)alkyl," as used herein, refers to a heterocyclic group, connected to the parent molecular moiety through an alkyl group. Representative examples of (heterocycle)alkyl include, but are not limited to, pyridin-3-ylmethyl and 2-pyrimidin-2-ylpropyl. The heterocycles of this invention can be optionally substituted with 1, 2, or 3 substituents independently selected from alkanoyl, alkenyl, alkoxy, alkoxyalkoxy, alkoxyalkyl, alkoxycarbonyl, alkyl, alkylsulfonyl, alkylthio, alkynyl, amino, aminoalkyl, aminocarbonyl, aminosulfonyl, carboxy, carboxyalkyl, cyano, cyanoalkyl, formyl, halogen, haloalkoxy, haloalkyl, hydroxy, hydroxyalkyl, mercapto, and nitro.

The term "(heterocycle)alkynyl," as used herein, refers to a heterocyclic group, connected to the parent molecular moiety through an alkynyl group. The heterocycles of this invention can be optionally substituted with 1, 2, or 3 substituents independently selected from alkanoyl, alkenyl, alkoxy, alkoxyalkoxy, alkoxyalkyl, alkoxycarbonyl, alkyl, alkylsulfonyl, alkylthio, alkynyl, amino, aminoalkyl, aminocarbonyl, aminosulfonyl, carboxy, carboxyalkyl, cyano, cyanoalkyl, formyl, halogen, haloalkoxy, haloalkyl, hydroxy, hydroxyalkyl, mercapto, and nitro.

The term "(heterocycle)amino," as used herein, refers to a heterocyclic group, connected to the parent molecular moiety through an amino group.

The term "(heterocycle)aminocarbonyl," as used herein, refers to a (heterocycle)amino group, connected to the parent molecular moiety through a carbonyl group.

The term "(heterocycle)carbonyl," as used herein, refers to a heterocyclic group, connected to the parent molecular moiety through a carbonyl group. The heterocycles of this invention can be optionally substituted with 1, 2, or 3 substituents independently selected from alkanoyl, alkenyl, alkoxy, alkoxyalkoxy, alkoxyalkyl, alkoxycarbonyl, alkyl, alkylsulfonyl, alkylthio, alkynyl, amino, aminoalkyl, aminocarbonyl, aminosulfonyl, carboxy, carboxyalkyl, cyano, cyanoalkyl, formyl, halogen, haloalkoxy, haloalkyl, hydroxy, hydroxyalkyl, mercapto, and nitro.

The term "(heterocycle)oxy," as used herein, refers to a heterocyclic group, connected to the parent molecular moiety through an oxygen atom.

The term "(heterocycle)oxycarbonyl," as used herein, refers to a (heterocycle)oxy group, connected to the parent molecular moiety through a carbonyl group.

The term "(heterocycle)thio," as used herein, refers to a heterocyclic group, connected to the parent molecular moiety through a sulfur atom.

The term "(heterocycle)thiocarbonyl," as used herein, refers to a (heterocycle)thio group, connected to the parent molecular moiety through a carbonyl group.

The term "(heterocycle)sulfonyl," as used herein, refers to a heterocyclic group, connected to the parent molecular moiety through a sulfonyl group. The heterocycles of this invention can be optionally substituted with 1, 2, or 3 substituents independently selected from alkanoyl, alkenyl, alkoxy, alkoxyalkoxy, alkoxyalkyl, alkoxycarbonyl, alkyl, alkylsulfonyl, alkylthio, alkynyl, amino, aminoalkyl, aminocarbonyl, aminosulfonyl, carboxy, carboxyalkyl, cyano, cyanoalkyl, formyl, halogen, haloalkoxy, haloalkyl, hydroxy, hydroxyalkyl, mercapto, and nitro.

The term "heterocyclene," as used herein, refers to a diradical formed by the removal of two hydrogen atoms from a heterocycle, above. Representative examples of heterocyclene include, but are not limited to, pyrrolidin-2,4-diyl, pyrrolidin-1,4-diyl, and isoxazol-3,5-diyl. The heterocyclene groups of this invention are divalent and can be connected through either two different carbon atoms or a carbon atom and a nitrogen atom in the ring.

The terms "hydroxyl," and "hydroxy," as used herein, refers to —OH or a derivative thereof formed by replacement of the hydrogen atom thereon with a hydroxyl protecting group.

The term "hydroxyl protecting group," as used herein, refers to selectively introducible and removable groups, which protect hydroxyl groups against undesirable side reactions during synthetic procedures. Examples of hydroxyl protecting groups include groups such as benzyloxycarbonyl; 4-nitrobenzyloxycarbonyl; 4-bromobenzyloxycarbonyl; 4-methoxybenzyloxycarbonyl; methoxycarbonyl; tert-butoxycarbonyl; isopropoxycarbonyl; diphenylmethoxycarbonyl; 2,2,2-trichloroethoxycarbonyl; 2-(trimethylsilyl)ethoxycarbonyl; 2-furfuryloxycarbonyl; allyloxycarbonyl; alkanoyl; formyl; acetyl, chloroacetyl; trifluoroacetyl; methoxyacetyl; phenoxyacetyl; benzoyl; methyl; tert-butyl; 2,2,2-trichloroethyl; 2-trimethylsilylethyl; 1,1-dimethyl-2-propenyl; 3-methyl-3-butenyl; allyl; benzyl; para-methoxybenzyldiphenylmethyl; triphenylmethyl (trityl); tetrahydrofuryl; tetrahydropyranyl; methoxymethyl; methylthiomethyl; benzyloxymethyl; 2,2,2-trichloroethoxymethyl; 2-(trimethylsilyl)ethoxymethyl; methanesulfonyl; para-toluenesulfonyl; trimethylsilyl; tert-butyldimethylsilyl, triethylsilyl; triisopropylsilyl, and the like.

The term "hydroxyalkyl," as used herein, refers to a hydroxy group, connected to the parent molecular moiety through an alkyl group.

The term "mercapto," as used herein, refers to an —SH group.

The term "nitro," as used herein, refers to an —NO$_2$ group.

The term "oxo," as used herein, refers to a =O moiety.

The term "perfluoroalkoxy," as used herein, refers to a perfluoroalkyl group, connected to the parent molecular moiety through an oxygen atom.

The term "perfluoroalkyl," as used herein, refers to an alkyl group, in which all of the hydrogen atoms have been replaced with fluoride atoms.

The term "reducing agent," as used herein, refers to reagents capable of donating hydrogen atoms during the course of a chemical reaction. Examples of reducing agents include sodium cyanoborohydride, titanium (III) chloride-sodium cyanoborohydride, sodium borohydride, lithium aluminum hydride, diborane, borane complexes, hydrogen and platinum catlyst, hydrogen and palladium catalyst, and hydrogen and Raney® nickel.

The term "sulfonyl," as used herein, refers to an —SO$_2$— group.

It is intended that the definition of any substituent or variable at a particular part in a molecule be independent of its definition elsewhere in the molecule. Thus, for example, substituents such as —(CH$_2$)$_a$C(O)R$^8$ represent —CH$_2$C(O)H, and —CH$_2$C(O)CH$_3$; and substituents such as —(CH$_2$)$_a$N(R$^8$)C(O)N(R$^8$)$_2$ represent CH$_2$CH$_2$N(H)C(O)N(CH$_3$)(C$_3$H$_7$) and —CH$_2$N(CH$_3$)C(O)NH(CH$_3$), and the like.

The term "therapeutically acceptable salt," as used herein, represents salts or zwitterionic forms of the compounds which are water or oil-soluble or dispersible and are suitable for ailments and or diseases without undue toxicity, irritation, and allergic response, which are commensurate with a reasonable benefit/risk ratio, and which are effective for their intended use. The salts may be prepared during the final isolation and purification of the compounds or separately by reacting a free base group with a suitable acid. Representative acid addition salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, fumarate, hydrochloride, hydrobromide, hydroiodide, 2-hydroxyethansulfonate (isethionate), lactate, maleate, mesitylenesulfonate, methanesulfonate, naphthylenesulfonate, nicotinate, 2-naphthalenesulfonate, oxalate, pamoate, pectinate, persulfate, 3-phenylpropionate, picrate, pivalate, propionate, succinate, tartrate, thiocyanate, trichloroacetic, trifluoroacetic, phosphate, glutamate, bicarbonate, para-toluenesulfonate, and undecanoate. Also, the basic nitrogen-containing groups can be quaternized with alkyl halides such as methyl, ethyl, propyl, and butyl chlorides, bromides and iodides; dialkyl sulfates such as dimethyl, diethyl, dibutyl, and diamyl sulfates; long chain halides such as decyl, lauryl, myristyl, and stearyl chlorides, bromides, and iodides; arylalkyl halides such as benzyl and phenethyl bromides. Examples of acids which may be employed to form therapeutically acceptable acid addition salts include inorganic acids such as hydrochloric, hydrobromic, sulfuric, and phosphoric and organic acids such as oxalic, maleic, succinic, and citric.

Basic addition salts can be prepared during the final isolation and purification of the compounds by reacting a carboxylic acid-containing group with a suitable base such as the hydroxide, carbonate, or bicarbonate of a metal cation or with ammonia or an organic primary, secondary or tertiary amine. Therapeutically acceptable salts include cations based on alkali metals or alkaline earth metals such as lithium, sodium, potassium, calcium, magnesium, and aluminum salts and nontoxic quaternary ammonia and amine cations such as ammonium, tetramethylammonium, tetraethylammonium, methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine. Other representative organic amines useful for the formation of base addition salts include ethylenediamine, ethanolamine, diethanolamine, piperidine, and piperazine.

Asymmetric centers can exist in the compounds of this invention. This invention contemplates stereoisomers and mixtures thereof. Individual stereoisomers of compounds are prepared by synthesis from starting materials containing the chiral centers or by preparation of mixtures of enantiomeric products followed by separation such as conversion to a mixture of diastereomers followed by separation or recrystallization, chromatographic techniques, or direct separation of the enantiomers on chiral chromatographic columns. Starting compounds of particular stereochemistry are either commercially available or are made by the methods described herein and resolved by techniques well-known in the art.

Geometric isomers can exist in the compounds of this invention. This invention contemplates the various geometric isomers and mixtures thereof which result from the disposal of substituents around a carbon-carbon double bond. Substituents around a carbon-carbon double bond are designated as being of Z or E configuration, wherein the term "Z" refers to higher order substituents on the same side of the carbon-carbon double bond, and the term "E" refers to higher order substituents on opposite sides of the carbon-carbon double bond. A thorough discussion of E and Z isomerism is provided in J. March, *Advanced Organic Chemistry. Reactions, Mechanisms, and Structure*, 4th ed., John Wiley & Sons, New York, 1992, pp. 127–130.

The compounds of this invention can exist as therapeutically acceptable prodrugs. The term "therapeutically acceptable prodrug," as used herein, represents those prodrugs of the compounds of this invention which are, within the scope of sound medical judgment, suitable for use in contact with the tissues of humans and lower animals without undue toxicity, irritation, allergic response, and the like, commensurate with a reasonable benefit/risk ratio, and effective for their intended use, as well as the zwitterionic forms, where possible, of the compounds of this invention.

The term "prodrug," as used herein, represents compounds, which are rapidly transformed in vivo to the parent compound of the above formula (I) or formula (II), for example, by hydrolysis in blood.

Representative compounds of the present invention include, but are not limited to:

compound of formula (I): $R^1$ is $CH_2CH=CH_2$; $R^2$ is hydrogen; $R^3$ is hydrogen; $R^4$ is hydrogen; $R^5$ is hydrogen; $R^6$ is hydrogen; $R^p$'s hydrogen;

compound of formula (I): $R^1$ is hydrogen; $R^2$ is hydrogen; $R^3$ is hydrogen; $R^4$ and $R^5$ together are —C(O)—; $R^6$ is hydrogen; $R^p$ is hydrogen;

compound of formula (I): $R^1$ and $R^2$ together are —C(O)—; $R^3$ is hydrogen; $R^4$ and $R^5$ together are —C(O)—; and $R^6$ is $C(O)CH_3$; $R^p$ is hydrogen;

compound of formula (I): $R^1$ is hydrogen; $R^2$ is $C_6H_5CH_2CH_2CH_2$; $R^3$ is hydrogen; $R^4$ and $R^5$ together are —C(O)—; and $R^6$ is hydrogen; $R^p$ is hydrogen;

compound of formula (I): $R^1$ is (quinolin-3-yl)CH=CHCH$_2$; $R^2$ is $C(CH_3)_3OC(O)$; $R^3$ is hydrogen; $R^4$ is hydrogen; $R^5$ is hydrogen; $R^6$ is $C(O)CH_3$; $R^p$ is hydrogen;

compound of formula (II): $R^1$ is (quinolin-3-yl)CH=CHCH$_2$; $R^2$ is methoxy; $R^3$ is hydrogen; $R^4$ is hydrogen; $R^5$ is hydrogen; $R^p$ is hydrogen;

compound of formula (II): $R^1$ is (quinolin-3-yl)CH=CHCH$_2$; $R^2$ is hydrogen; $R^3$ is hydrogen; $R^4$ is hydrogen; $R^5$ is hydrogen; $R^p$ is hydrogen;

compound of formula (II): $R^1$ is (quinolin-3-yl)CH=CHCH$_2$; $R^2$ is hydrogen; $R^3$ and $R^4$ together are —C(O)—; $R^5$ is hydrogen; $R^p$ is hydrogen;

compound of formula (II): $R^1$ is (quinolin-3-yl)CH=CHCH$_2$; $R^2$ is hydrogen; $R^3$ is hydrogen; $R^4$ and $R^5$ are —C(O)—; $R^p$ is hydrogen; and compound of formula (II): $R^1$ is (quinolin-3-yl)CH=CHCH$_2$; $R^2$ is hydrogen; $R^3$ and $R^4$ together are —CH$_2$—; $R^5$ is hydrogen; $R^p$ is hydrogen.

The pharmaceutical compositions of the present invention comprise a therapeutically effective amount of a compound of the present invention, or a therapeutically acceptable salt or prodrug thereof, formulated together with one or more therapeutically acceptable carriers. As used herein, the term "therapeutically acceptable carrier" means a non-toxic, inert solid, semi-solid or liquid filler, diluent, encapsulating material or formulation auxiliary of any type. Some examples of materials which can serve as therapeutically acceptable carriers are sugars such as lactose, glucose, and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols, such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate. Coloring agents, releasing agents, coating agents, sweetening, flavoring, and perfuming agents, preservatives, and antioxidants can also be present in the composition, according to the judgment of the formulator.

In accordance with pharmaceutical compositions, methods of treatment, use as medicaments and as medicaments, the compounds can be administered alone to achieve an antibacterial effect or in combination with other antibacterial agents. Bacterial infections are treated or prevented in a patient such as a human or lower mammal by administering to the patient a therapeutically effective amount of a compound of the present invention, or a therapeutically acceptable salt or prodrug thereof, in such amounts and for such time as is necessary to achieve the desired result. By a "therapeutically effective amount" of a compound of the invention is meant a sufficient amount of the compound to treat bacterial infections, at a reasonable benefit/risk ratio applicable to any medical treatment. It will be understood, however, that the total daily usage of the compounds and compositions of the present invention will be decided by the attending physician within the scope of sound medical judgment. When using the compounds as antibacterial agents, the specific therapeutically effective amount or dose level for any particular patient will depend upon a variety of factors such as the disorder being treated and the severity of the disorder; the activity of the particular compound used; the specific composition employed; the age, body weight, general health, sex, and diet of the patient; the time of administration; the route of administration; the rate of excretion of the compound employed; the duration of treatment; and drugs used in combination with or coincidently with the compound used; and like factors well known in the medical arts. The compounds can be administered orally, parenterally, osmotically (nasal sprays), rectally, vaginally, or topically in unit dosage formulations containing carriers, adjuvants, diluents, vehicles, or combinations thereof. The term "parenteral" includes infusion as well as subcutaneous, intravenous, intramuscular, and intrasternal injection.

Parenterally administered aqueous or oleaginous suspensions of the compounds can be formulated with dispersing, wetting, or suspending agents. The injectable preparation can also be an injectable solution or suspension in a diluent or solvent. Among the acceptable diluents or solvents employed are water, saline, Ringer's solution, buffers, dilute acids or bases, dilute amino acid solutions, monoglycerides, diglycerides, fatty acids such as oleic acid, and fixed oils such as monoglycerides or diglycerides.

The antibacterial activity of parenterally administered compounds can be prolonged by slowing their absorption. One way to slow the absorption of a particular compound is administering injectable depot forms comprising suspensions of crystalline, amorphous, or otherwise water-insoluble forms of the compound. The rate of absorption of the compound is dependent on its rate of dissolution, which is, in turn, dependent on its physical state. Another way to slow absorption of a particular compound is administering injectable depot forms comprising the compound as an oleaginous solution or suspension. Yet another way to slow absorption of a particular compound is administering injectable depot forms comprising microcapsule matrices of the compound trapped within liposomes, microemulsions, or biodegradable polymers such as polylactide-polyglycolide, polyorthoesters or polyanhydrides. Depending on the ratio of drug to polymer and the composition of the polymer, the rate of drug release can be controlled.

Transdermal patches also provide controlled delivery of the compounds. The rate of absorption can be slowed by using rate-controlling membranes or by trapping the compound within a polymer matrix or gel. Conversely, absorption enhancers can be used to increase absorption.

Solid dosage forms for oral administration include capsules, tablets, pills, powders, and granules. In these solid dosage forms, the active compound can optionally comprise diluents such as sucrose, lactose, starch, talc, silicic acid, aluminum hydroxide, calcium silicates, polyamide powder, tableting lubricants, and tableting aids such as magnesium stearate or microcrystalline cellulose. Capsules, tablets and pills can also comprise buffering agents; and tablets and pills can be prepared with enteric coatings or other release-controlling coatings. Powders and sprays can also contain excipients such as talc, silicic acid, aluminum hydroxide, calcium silicate, polyamide powder, or mixtures thereof. Sprays can additionally contain customary propellants such as chlorofluorohydrocarbons or substitutes therefore.

Liquid dosage forms for oral administration include emulsions, microemulsions, solutions, suspensions, syrups, and elixirs comprising inert diluents such as water. These compositions can also comprise adjuvants such as wetting, emulsifying, suspending, sweetening, flavoring, and perfuming agents.

Topical dosage forms include ointments, pastes, creams, lotions, gels, powders, solutions, sprays, inhalants, and transdermal patches. The compound is mixed under sterile conditions with a carrier and any needed preservatives or buffers. These dosage forms can also include excipients such as animal and vegetable fats, oils, waxes, paraffins, starch, tragacanth, cellulose derivatives, polyethylene glycols, silicones, bentonites, silicic acid, talc and zinc oxide, or mixtures thereof. Suppositories for rectal or vaginal administration can be prepared by mixing the compounds with a suitable nonirritating excipient such as cocoa butter or polyethylene glycol, each of which is solid at ordinary temperature but fluid in the rectum or vagina. Ophthalmic formulations comprising eye drops, eye ointments, powders, and solutions are also contemplated as being within the scope of this invention.

The total daily dose of the compounds administered to a host in single or divided doses can be in amounts from about 0.1 to about 200 mg/kg body weight or preferably from about 0.25 to about 100 mg/kg body weight. Single dose compositions can contain these amounts or submultiples thereof to make up the daily dose.

Determination of Biological Activity

In Vitro Assay of Antibacterial Activity

Representative compounds of the present invention were assayed in vitro for antibacterial activity as follows: Twelve petri dishes containing successive aqueous dilutions of the test compound mixed with 10 mL of sterilized Brain Heart Infusion (BHI) agar (Difco 0418-01-5) were prepared. Each plate was inoculated with 1:100 (or 1:10 for slow-growing strains, such as Micrococcus and Streptococcus) dilutions of up to 32 different microorganisms, using a Steers replicator block. The inoculated plates were incubated at 35–37° C. for 20 to 24 hours. In addition, a control plate, using BHI agar containing no test compound, was prepared and incubated at the beginning and end of each test.

An additional plate containing a compound having known susceptibility patterns for the organisms being tested and belonging to the same antibiotic class as the test compound was also prepared and incubated as a further control, as well as to provide test-to-test comparability. Erythromycin A was used for this purpose.

After incubation, each plate was visually inspected. The minimum inhibitory concentration (MIC) was defined as the lowest concentration of drug yielding no growth, a slight haze, or sparsely isolated colonies on the inoculum spot as compared to the growth control. The results of this assay, shown below in Table 1, demonstrate the antibacterial activity of the compounds of the present invention.

TABLE 1

Antibacterial Activity of Selected Compounds (MIC's in µg/mL)

| Microorganism | Organism code | Ery. A standard |
|---|---|---|
| *Staphylococcus aureus* ATCC 6538P | AA | 0.2 |
| *Staphylococcus aureus* 1775 | BB | >100 |
| *Haemophilus influenzae* DILL AMP R | CC | 4 |
| *Streptococcus pyogenes* EES61 | DD | 0.06 |
| *Streptococcus pyogenes* 930 | EE | >128 |
| *Streptococcus pyogenes* PIU 2548 | FF | 32 |
| *Streptococcus pneumoniae* ATCC 6303 | GG | 0.06 |
| *Streptococcus pneumoniae* 5737 | HH | >128 |
| *Streptococcus pneumoniae* 5649 | JJ | 16 |

| Organism code | Example 3 | Example 7 | Example 8 | Example 9 |
|---|---|---|---|---|
| AA | 0.39 | 0.78 | 0.39 | 0.2 |
| BB | >100 | >100 | >100 | >100 |
| CC | 4 | 16 | 16 | 32 |
| DD | 0.12 | 0.25 | 0.03 | 1 |
| EE | >128 | —* | >128 | >128 |
| FF | 16 | 2 | 1 | >128 |
| GG | 0.12 | 0.5 | 0.03 | 2 |
| HH | >128 | >64 | 128 | >128 |
| JJ | 2 | 1 | 2 | 32 |

*missing data is indicated by "—"

Synthetic Methods

Abbreviations which have been used in the descriptions of the scheme and the examples that follow are: dppb for 1,4-bis(diphenylphosphino)butane, Ac for acetate; dba for dibenzylideneacetone, EtOAc for ethyl acetate, DCM for dichloromethane; DME for 1,2-dimethoxyethane; MeOH for methanol, EtOH for ethanol; THF for tetrahydrofuran; TEA for triethylamine; CDI for carbonyldiimidazole, DMAP for 4-(dimethylamino)pyridine; dioxane for 1,4-dioxane; Ac for acetate; $BOC_2O$ for di-tert-butyl dicarbonate; AcOH for acetic acid; TFA for trifluoroacetic acid; $P(o\text{-tolyl})_3$ for tris-ortho-tolylphosphine; TsOH for para-toluenesulfonic acid; DMSO for dimethylsulfoxide; CBzCl for carbobenzyloxy chloride; TMSCl for trimethylsilyl chloride; TBME for tert-butylmethyl ether; DBU for 1,8-diazabicyclo[5.4.0]undec-7-ene; DMF for N,N-dimethylformamide; LiHMDS for lithium bis(trimethylsilyl)amide; NaHMDS for sodium bis(trimethylsilyl)amide; KHMDS for potassium bis(trimethylsilyl)amide; NCS for N-chlorosuccinimide; EDCI for 1-(3-dimethylaminopropyl)-3-ethylcarbodiimide; PCC for pyridinium chlorochromate.

The compounds and processes of the present invention will be better understood in connection with the following synthetic schemes, which illustrate the methods by which the compounds of the invention may be prepared. It will be readily apparent to one of ordinary skill in the art that the compounds can be synthesized by substitution of the appropriate reactants in these syntheses, and that the steps themselves can be conducted in varying order. It will also be apparent that protection and deprotection steps can be performed to successfully complete the syntheses of the compounds. A thorough discussion of protecting groups is provided in T. W. Greene and P. G. M. Wuts, *Protective Groups in Organic Synthesis*, 3rd edition, John Wiley & Sons, New York (1999). The groups $R^1$, $R^2$, $R^3$, $R^4$, $R^5$, $R^6$, $R^7$, $R^8$, $R^9$, and $R^p$ are as defined hereinabove unless otherwise noted below.

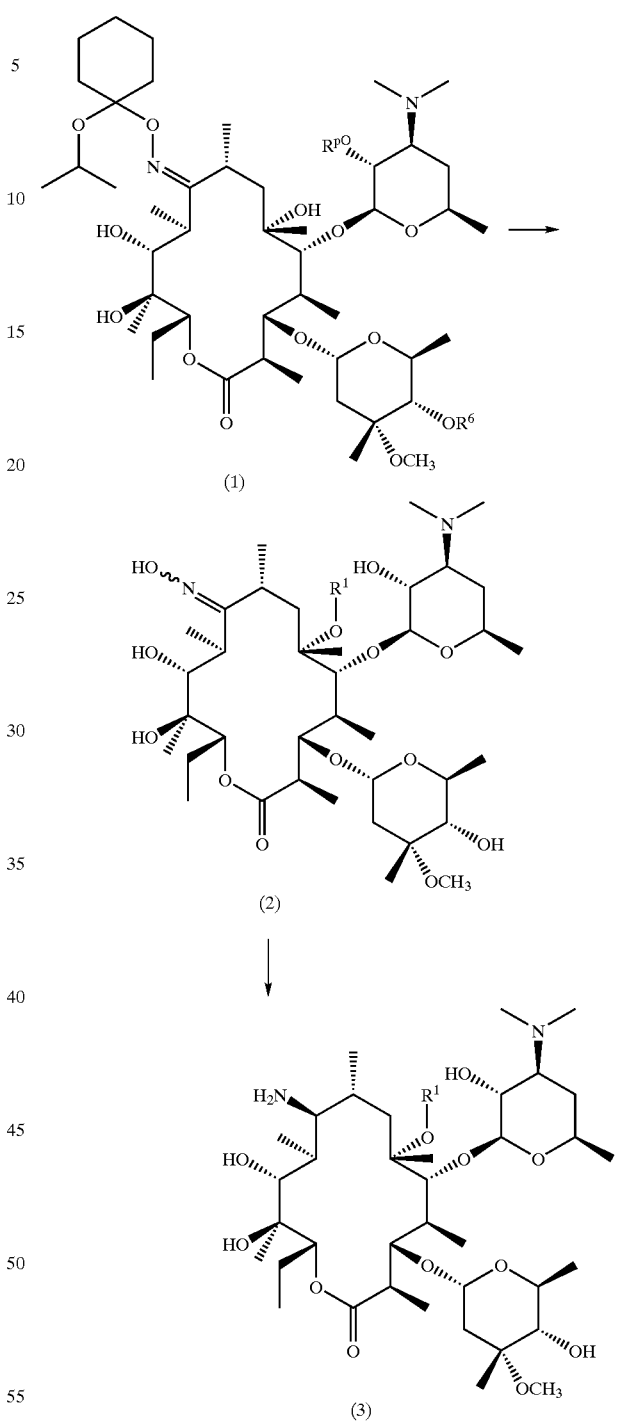

Scheme 1

As shown in Scheme 1, the conversion of (1), wherein $R^1$, $R^6$, and $R^p$ are defined above to (2) can be accomplished by treating the former with propenyl tert-butyl carbonate, $Pd_2(dba)_3$ and dppb to form an intermediate. The intermediate is then deprotected with acetic acid to form (2). Alternatively, (2) can be obtained by treating (1) with allyl bromide in the presence of a base, followed by deprotection. Examples of bases include potassium hydroxide and potassium tert-butoxide.

The conversion of (2) to (3) can be accomplished by treating the former with a reducing agent and an additive in an optionally buffered solvent. Specific examples of reducing agents include $NaCNBH_3$, $TiCl_3\text{-}NaCNBH_3$, $LiAlH_4$, $NaBH_4$, diborane, borane complexes, hydrogen gas, $AlH_3$ and $NaBH_2S_3$. Specific examples of additives include acetic acid, hydrochloric acid, $TiCl_3$, $TiCl_4$, $MoO_3$, $NiCl_2$, tartaric acid, palladium on carbon, platinum oxide, and Raney® nickel. Specific examples of buffering agents include $NH_4OAc$, $NaOAc$, $KH_2PO_4$, and $K_2HPO_4$. Specific examples of solvents include THF, TBME, MeOH, EtOH, isopropanol, and n-propanol. Although the reaction generally proceeds at room temperature, it can be run at lower or elevated temperatures, as needed. The reaction time is generally about three hours to about 36 hours.

Scheme 2

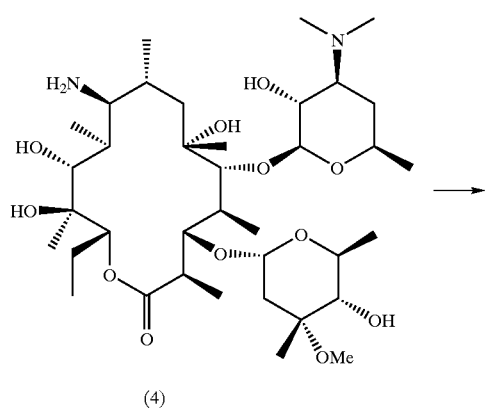

(4)

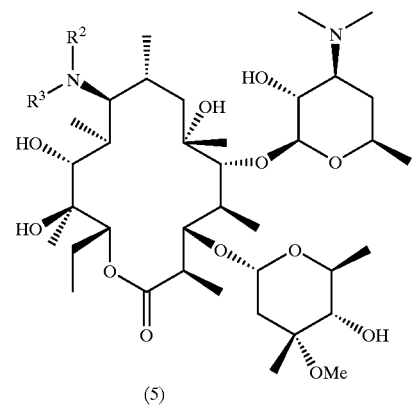

(5)

As shown in Scheme 2, the conversion of (4), wherein $R^2$ and $R^3$ are defined above, to (5) can be accomplished by treating the former with an acylating agent, an aldehyde, a ketone or an alkylating agent, and an additive in a solvent. More preferred are CBzCl, N-(benzyloxycarbonyl) succinimide, di-tert-butyl dicarbonate, formaldehyde, hydrocinnamaldehyde, and 4-(4'-quinolyl)butyraldehyde. Specific examples of additives include acids, bases, reducing agents and mixtures thereof. Specific examples of bases include TEA, lutidine, pyridine, and diisopropylethylamine. Specific examples of acids include HCl, triflic acid, TsOH, and acetic acid. Specific examples of solvents include MeOH, EtOH, THF, dioxane, and DCM. Although the reaction generally proceeds at room temperature, it can be run at lower or elevated temperatures. The reaction time is generally about three hours to about 24 hours.

Scheme 3

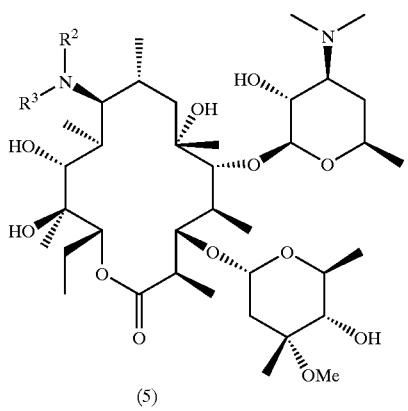

(5)

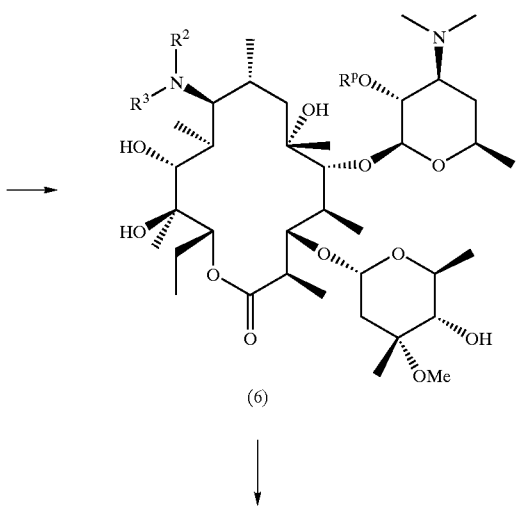

(6)

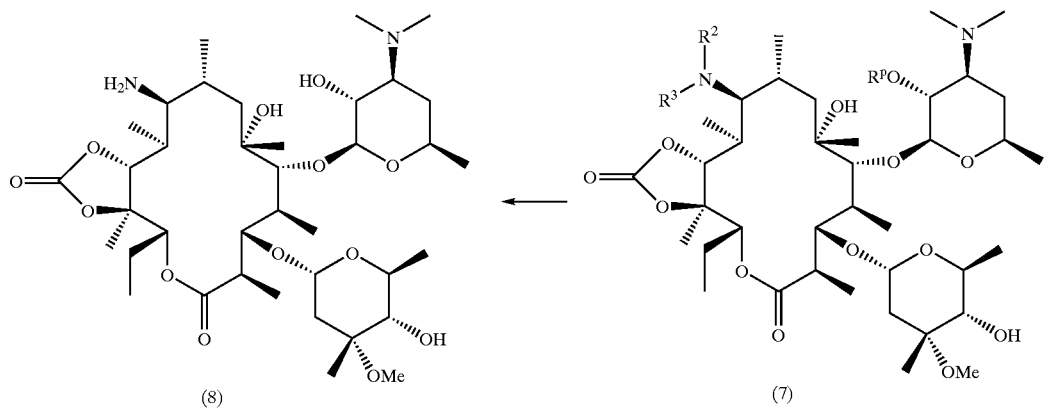

(8)        (7)

As shown in Scheme 3, the conversion of (5), wherein $R^2$, $R^3$, and $R^P$ are defined amine in a solvent. Specific examples of protecting group precursors include TMSCl, benzoic anhydride and acetic anhydride. Specific examples of amines include TEA, diisopropylethylamine, pyridine, and lutidine. Specific examples of solvents include dioxane, THF, DCM, chloroform, TBME, DME, and mixtures thereof. Although the reaction generally proceeds at room temperature, it can be run at lower or elevated temperatures as needed. The reaction time is generally about four hours to about 24 hours.

The conversion of (6) to (7) can be accomplished by treating the former with phosgene or triphosgene and a base in a solvent. Specific examples of bases include pyridine, lutidine, DBU, TEA, and diisopropylethylamine. Specific examples of solvents include DCM, chloroform, THF, and dioxane. Although the reaction generally proceeds at −70° C., it can be run at elevated temperatures as needed. The reaction time is generally about two hours to about 16 hours.

The conversion of (7) to (8) can be accomplished by treating the former with a deprotecting agent in a nucleophilic solvent. Specific examples of deprotecting agents include hydrogen gas and Pd/C; tert-butyldimethylsilane, TEA and Pd(OAc)$_2$, and AcOH and HBr. Specific examples of nucleophilic solvents include MeOH and EtOH. The reaction generally proceeds at room temperature, but can be run at elevated temperatures. The reaction time is generally about one hour to about 16 hours.

Scheme 4

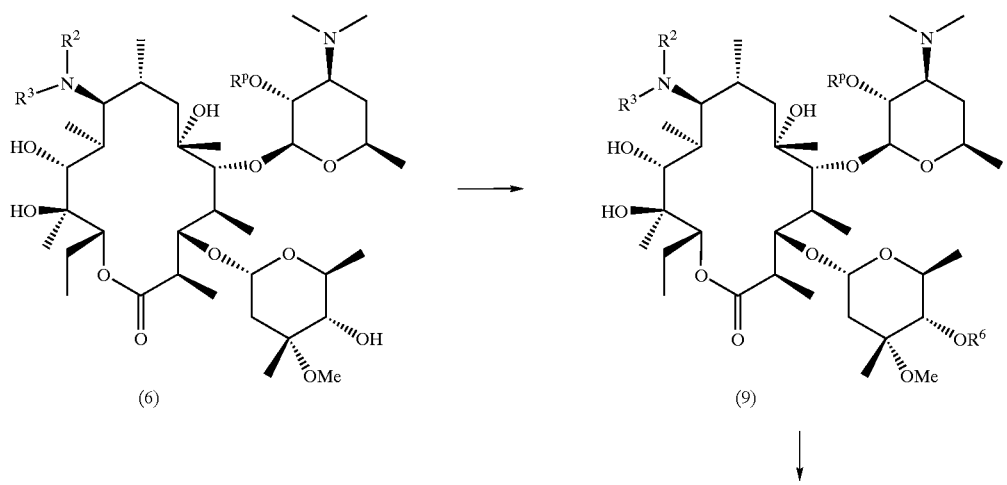

(6)        (9)

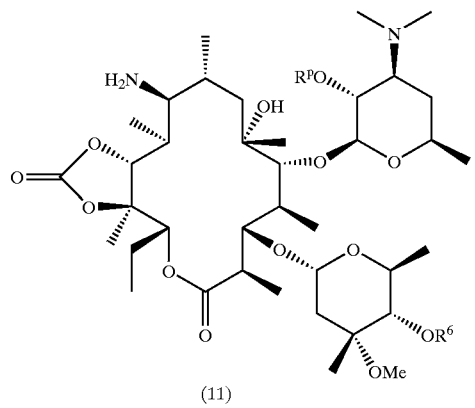

(11)

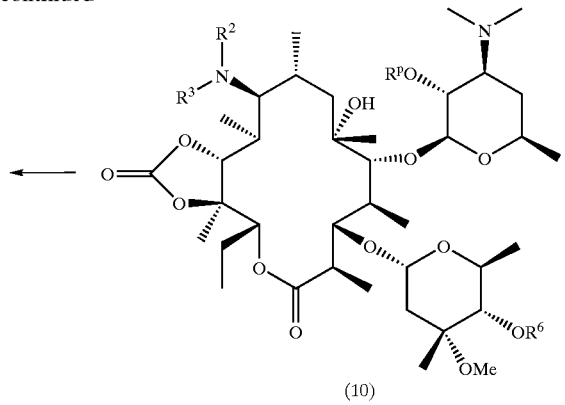

(10)

As shown in Scheme 4, the conversion of (6) wherein $R^2$, $R^3$, $R^6$, and $R^p$ are defined above, to (9) can be accomplished be treating the former with a protecting group precursor, an amine and a second amine in a solvent. Specific examples of protecting group precursors include TMSCl, and acetic anhydride. Specific examples of amines include TEA, diisopropylethylamine, pyridine, and lutidine. A specific example of a second amine is DMAP. Specific examples of solvents include dioxane, THF, DCM, chloroform, TBME, DME, and mixtures thereof. Although the reaction generally proceeds at room temperature, it can be run at lower or elevated temperatures as needed. The reaction time is generally about four hours to about 24 hours.

The conversion of (9) to (10) can be accomplished by treating the former with phosgene or triphosgene and a base in a solvent. Specific examples of bases include pyridine, lutidine, DBU, TEA, and diisopropylethylamine. Specific examples of solvents include DCM, chloroform, THF, and dioxane. Although the reaction generally proceeds at −70° C., it can be run at elevated temperatures as needed. The reaction time is generally about two hours to about 16 hours.

The conversion of (10) to (11) can be accomplished by treating the former with a deprotecting agent in a nucleophilic solvent. Specific examples of deprotecting agents include hydrogen gas and Pd/C; tert-butyldimethylsilane, TEA and Pd(OAc)$_2$, and AcOH and HBr. Specific examples of nucleophilic solvents include MeOH and EtOH. The reaction generally proceeds at room temperature, but can be run at elevated temperatures. The reaction time is generally about one hour to about 16 hours.

Scheme 5

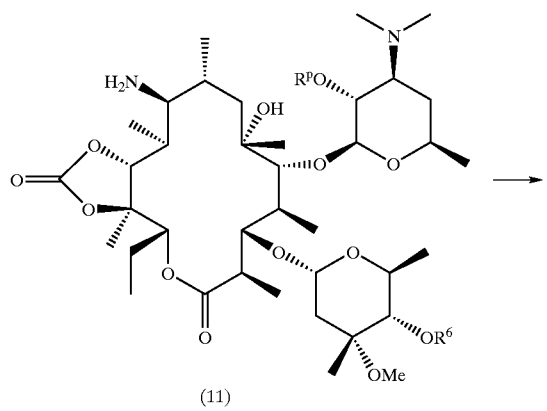

(11)

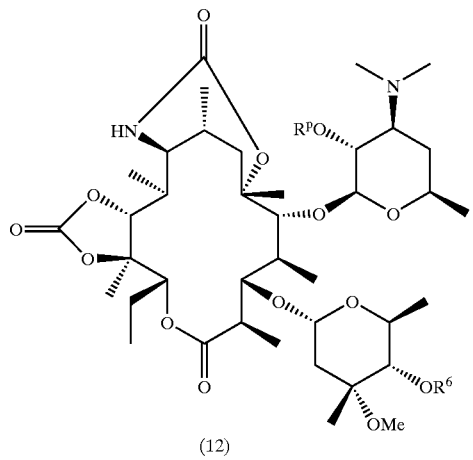

(12)

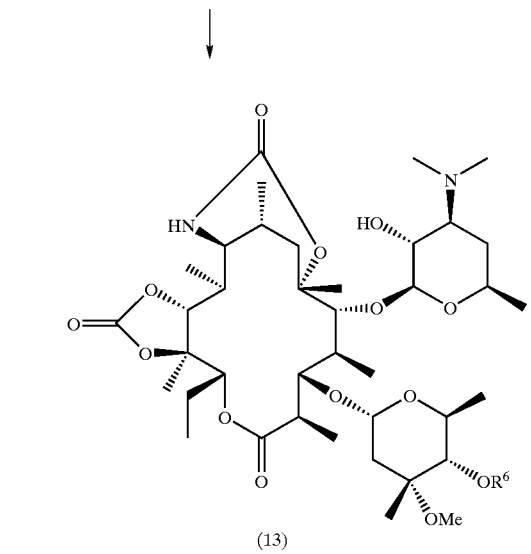

(13)

As shown in Scheme 5, the conversion of (11), wherein $R^6$ and $R^p$ are defined above, to (12) can be accomplished by treating the former with a carbonyl source and a base in a solvent. Specific examples of carbonyl sources include phosgene, triphosgene and CDI. Specific examples of bases include NaH, KH, LiHMDS, NaHMDS, and KHMDS.

Specific examples of solvents include THF, DME, TBME, DMSO and DMF. Although the reaction generally proceeds at elevated temperatures, it can be run at lower temperatures. The reaction time is generally about 0.5 hours to about 8 hours.

The conversion of (12) to (13) can be accomplished by treating the former with nucleophilic solvent. Specific examples of nucleophilic solvents include MeOH and EtOH. Although the reaction temperature is generally room temperature, it can be run at elevated temperatures. The reaction time is generally about 2 hours to about 60 hours.

Scheme 6

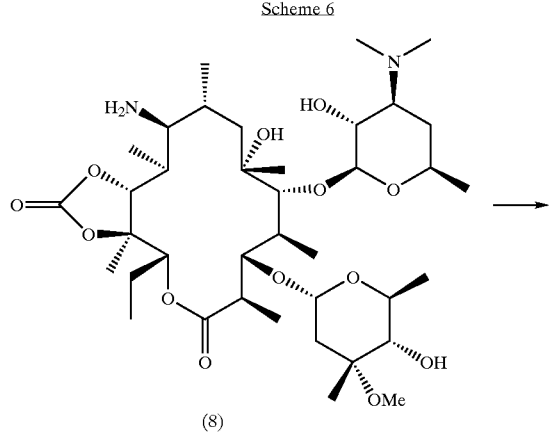

(8)

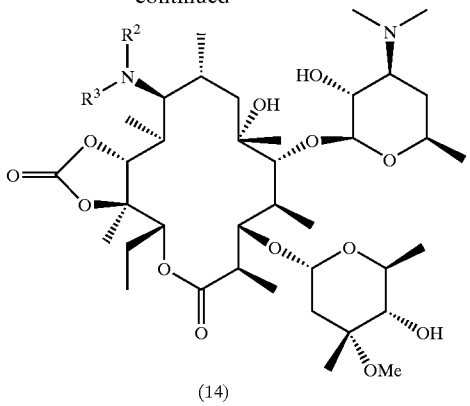

(14)

As shown in Scheme 6, the conversion of (8), wherein $R^2$ and $R^3$ are defined above, to (14) can be accomplished by treating the former with an acylating agent, an aldehyde, a ketone or an alkylating agent, and an additive in a solvent. More preferred are CBzCl, N-(benzyloxycarbonyl) succinimide, di-tert-butyl dicarbonate, formaldehyde, hydrocinnamaldehyde, and 4-(4'-quinolyl)butyraldehyde. Specific examples of additives include acids and bases. Specific examples of bases include TEA, lutidine, pyridine, and diisopropylethylamine. Specific examples of acids include HCl, triflic acid, TsOH, and acetic acid. Specific examples of solvents include MeOH, EtOH, THF, dioxane, and DCM. Although the reaction generally proceeds at room temperature, it can be run at lower or elevated temperatures. The reaction time is generally about three hours to about 24 hours.

Scheme 7

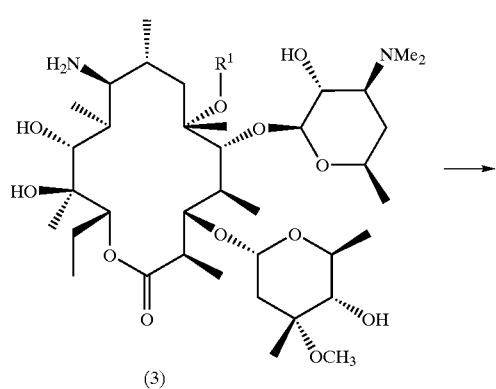

(3)

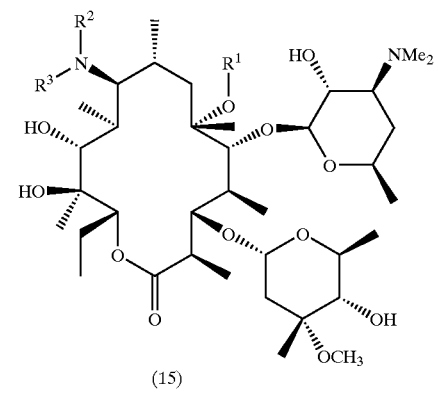

(15)

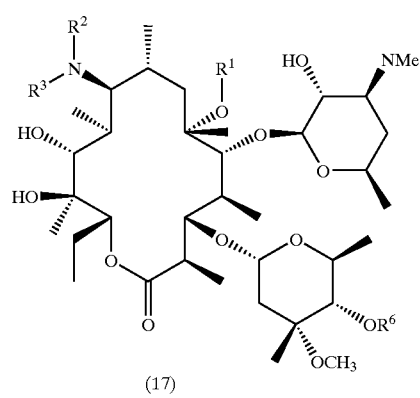

(17)

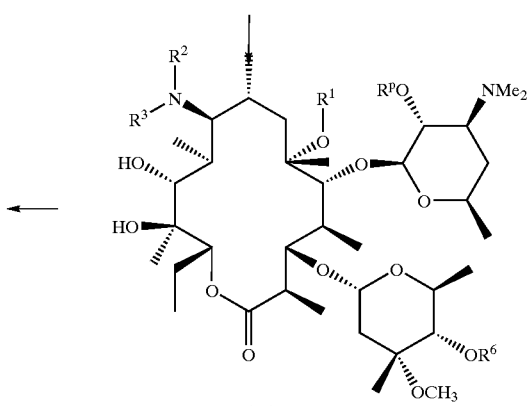

(16)

As shown in Scheme 7, the conversion of (3), wherein $R^1$, $R^2$, $R^3$, $R^6$, and $R^P$ are defined above, to (15) can be accomplished by treating the former with an acylating agent, an aldehyde, a ketone or an alkylating agent, and an additive in a solvent. More preferred are CBzCl, N-(benzyloxycarbonyl)succinimide, di-tert-butyl dicarbonate, formaldehyde, hydrocinnamaldehyde, and 4-(4'-quinolyl)butyraldehyde. Specific examples of additives include acids and bases. Specific examples of bases include TEA, lutidine, pyridine, and diisopropylethylamine. Specific examples of acids include HCl, triflic acid, TsOH, and acetic acid. Specific examples of solvents include MeOH, EtOH, THF, dioxane, and DCM. Although the reaction generally proceeds at room temperature, it can be run at lower or elevated temperatures. The reaction time is generally about three hours to about 24 hours.

The conversion of (15) wherein $R^1$, $R^2$, and $R^3$ are previously defined, to (16), wherein $R^P$ and $R^6$ are a previously defined hydroxyl protecting group can be accomplished by treating the former with a protecting group precursor, and an amine in a solvent. Specific examples of protecting group precursors include TMSCl, and acetic anhydride. Specific examples of amines include TEA, diisopropylethylamine, pyridine, and lutidine. Specific examples of solvents include dioxane, THF, DCM, chloroform, TBME, DME, and mixtures thereof. Although the reaction generally proceeds at room temperature, it can be run at lower or elevated temperatures as needed. The reaction time is generally about four hours to about 24 hours.

If $R^1$ is alkenyl or alkynyl, it can be elaborated by a transition metal catalyzed carbon-carbon bond forming reaction. In particular the alkene or alkyne can be elaborated by treatment with a transition metal catalyst, a base, an additive and an aryl halide in a solvent. Specific examples of transition metal catalysts include $Pd(PPh_3)_4$, $Pd(OAc)_2$, $PdCl_2(PPh_3)_2$, and $Pd_2(dba)_3 \cdot CHCl_3$. Specific examples of bases include N,N-diisopropylethylamine and TEA. Specific examples of additives include tetrabutylammonium bromide and tetrabutylammonium chloride. Specific examples of aryl halides include 3-bromoquinoline, 4-bromoquinoline, benzyl bromide and iodobenzene. The reaction generally proceeds at elevated temperatures. The reaction time is generally about four hours to about 36 hours.

The conversion of (16) to (17) can be accomplished by treating the former with a nucleophilic solvent. Specific examples of nucleophilic solvents include MeOH and EtOH. The reaction generally proceeds at room temperature, but can be run at elevated temperatures. The reaction time is generally about 2 hours to about 60 hours.

Scheme 8

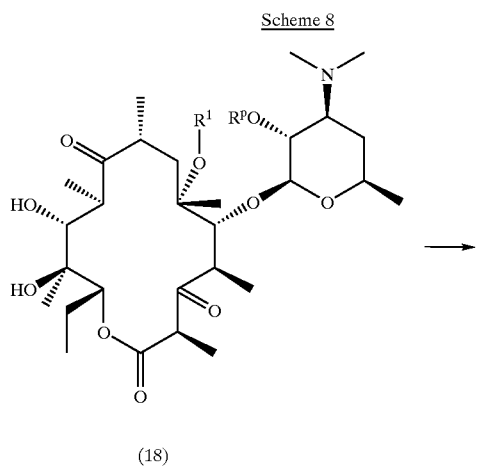

(18)

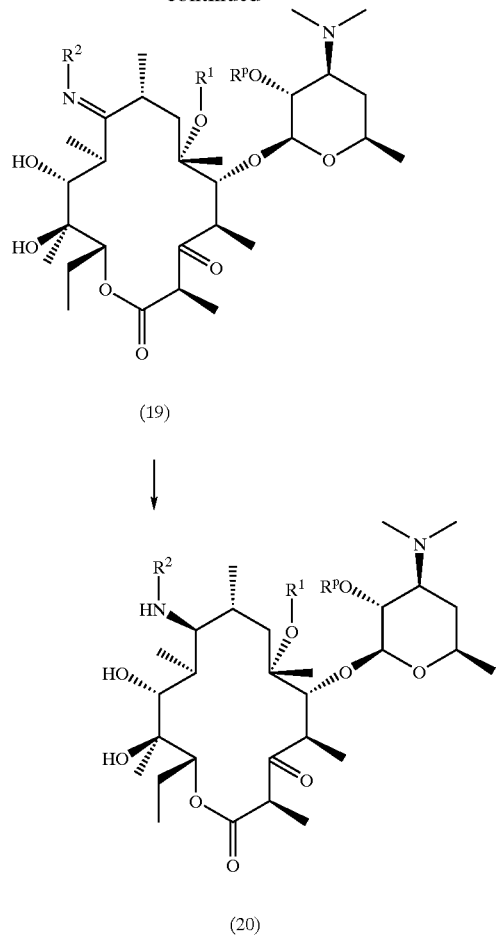

(19)

(20)

As shown in Scheme 8, the conversion of (18), wherein $R^1$, $R^2$, and $R^P$ are defined above, (prepared according to the procedure described in U.S. Pat. No. 5,866,549) to (19) can be accomplished by treating the former with a hydroxylamine, and an acid in a solvent. Specific examples of hydroxylamines include O-methylhydroxylamine hydrochloride, O-benzylhydroxylamine hydrochloride, hydroxylamine hydrochloride, N,O-dimethylhydroxylamine hydrochloride, O-ethylhydroxylamine hydrochloride. Specific examples of acids include acetic acid, TFA, triflic acid, TsOH and HCl. Specific examples of solvents include MeOH, EtOH, THF, and mixtures thereof. The reaction is generally carried out at reflux, the temperature of which can be determined by the solvent mixture that is used. The reaction time is generally about 16 hours to about 6 days.

The conversion of (19), wherein $R^1$, $R^2$, and $R^P$ are defined above, to (20) can be accomplished by treating the former with an acid, and a reducing agent and in a solvent. Specific examples of acids include acetic acid, TFA, triflic acid, TsOH and HCl. Specific examples of reducing agents include $NaCNBH_3$, $NaCNBH_3$—$MoO_3$, $NaBH_4$, and hydrogen and palladium. Specific examples of solvents include MeOH, EtOH, THF, and mixtures thereof. Although the reaction is generally carried out at room temperature, it can be run at lower temperatures. The reaction time is generally about four hours to about 36 hours.

Scheme 9

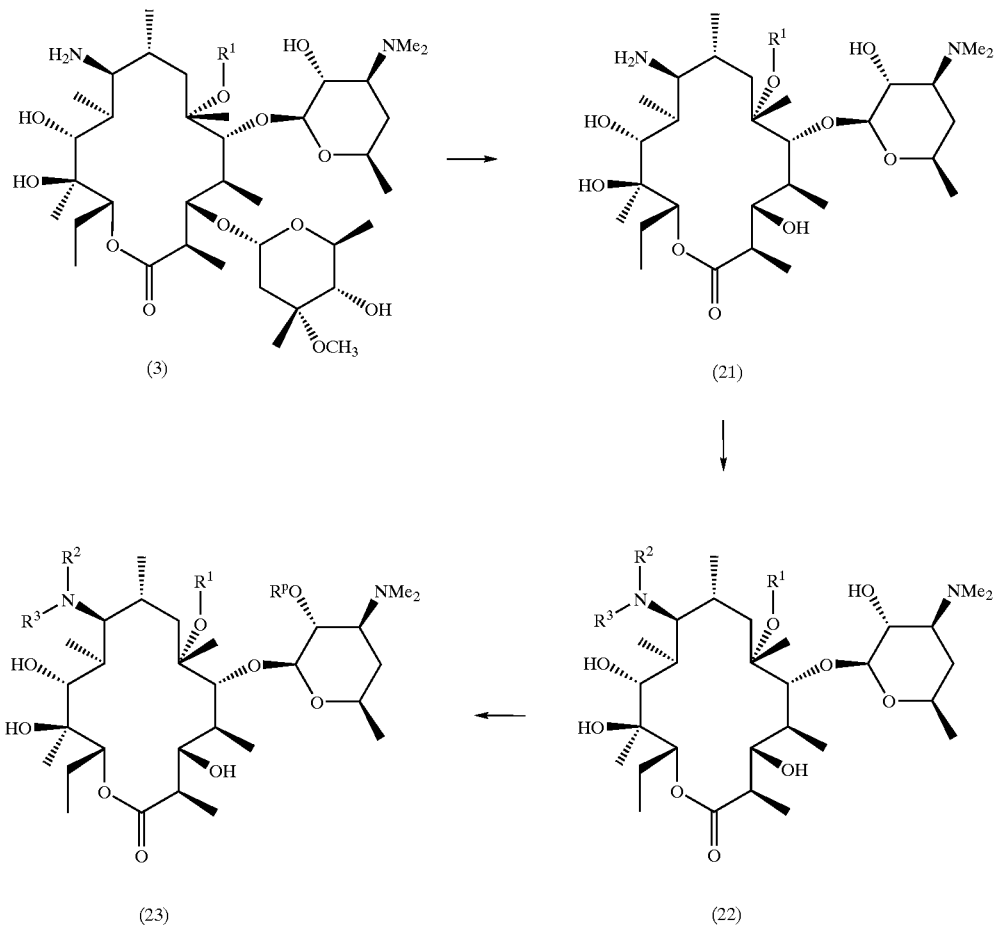

As shown in Scheme 9, the conversion of (3), wherein $R^1$, $R^2$, $R^3$, and $R^p$ are defined above, to (21) can be accomplished be treating the former with an acid in a solvent. Specific examples of solvents include HCl, triflic acid, TsOH, and TFA. Specific examples of solvents include water, MeOH, EtOH, acetone, THF, and mixtures thereof. Although the reaction is generally carried out at room temperature, it may be run at lower or elevated temperatures. The reaction time is generally 12 hours to about three days.

The conversion of (21) to (22) can be accomplished by treating the former with an acylating agent, an aldehyde, a ketone or an alkylating agent, and an additive in a solvent. More preferred are CBzCl, N-(benzyloxycarbonyl) succinimide, di-tert-butyl dicarbonate, formaldehyde, hydrocinnamaldehyde, and 4-(4'-quinolyl)butyraldehyde. Specific examples of additives include acids, bases, reducing agents, and mixtures thereof. Specific examples of bases include TEA, lutidine, pyridine, and diisopropylethylamine. Specific examples of acids include HCl, triflic acid, TsOH, and acetic acid. Specific examples of reducing agents include Na(CN)BH$_3$, NaBH$_4$, and hydrogen and palladium. Specific examples of solvents include MeOH, EtOH, THF, dioxane, and DCM. Although the reaction generally proceeds at room temperature, it can be run at lower or elevated temperatures. The reaction time is generally about three hours to about 24 hours.

The conversion of (22) to (23) can be accomplished by treating the former with a protecting group precursor, and an amine in a solvent. Specific examples of protecting group precursors include TMSCl, benzoic anhydride and acetic anhydride. Specific examples of amines include TEA, diisopropylethylamine, pyridine, and lutidine. Specific examples of solvents include dioxane, THF, DCM, chloroform, TBME, DME, and mixtures thereof. Although the reaction generally proceeds at room temperature, it can be run at lower or elevated temperatures as needed. The reaction time is generally about four hours to about 24 hours.

Scheme 10

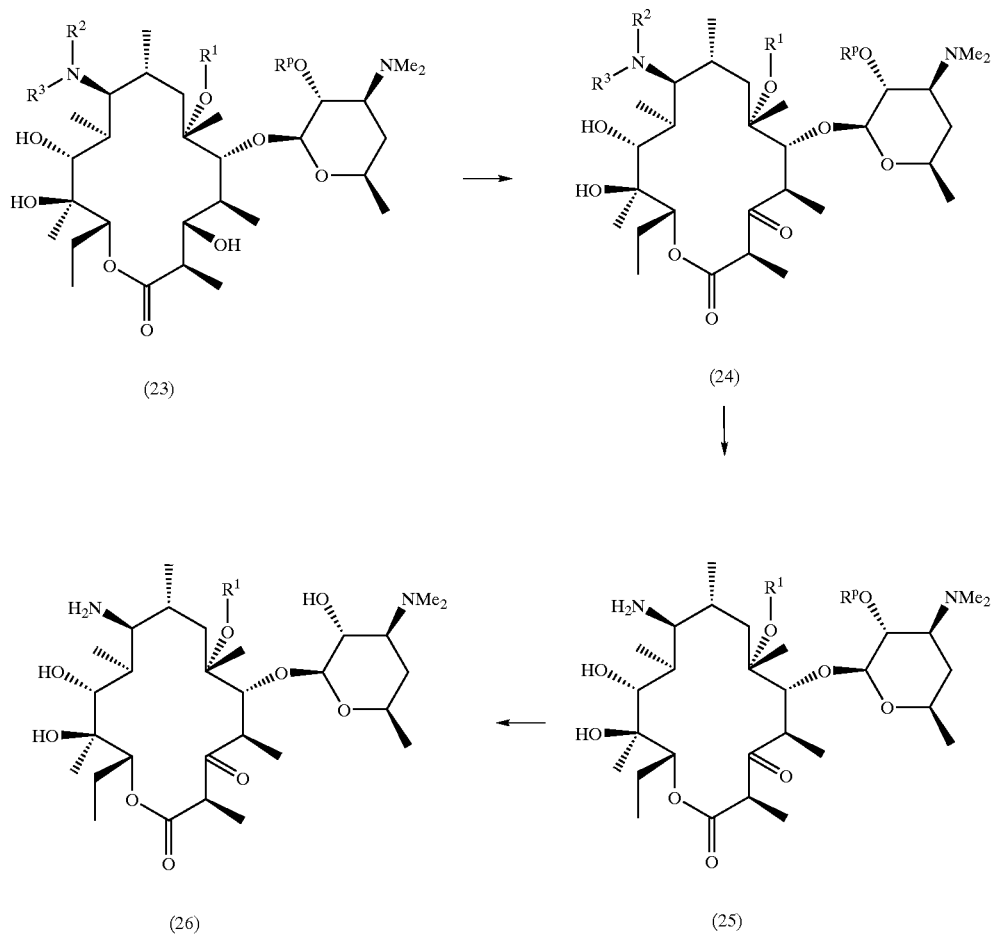

As shown in Scheme 10, the conversion of (23), wherein $R^1$, $R^2$, $R^3$, and $R^p$ are defined above, to (24) can be accomplished by treating the former with an oxidizing agent, and an optionally added additive in a solvent. Specific examples of oxidizing agents include DMSO and NCS, DMSO and EDCI, DMSO and oxalyl chloride, and PCC. Specific examples of additives include $H_3PO_4$, pyridinium trifluoroacetate, silica gel, TEA, and pyridine. Specific examples of solvents include DCM, THF, DMSO, and dioxane. Although the reaction generally proceeds at room temperature, it can be run at lower temperatures. The reaction time is generally about four hours to about 24 hours.

If $R^1$, $R^2$, or $R^3$ contain a double bond or a halide, the double bond or halide may be elaborated by means well known in the art. For example, alkenes and alkynes can be coupled to aromatic halides and triflates by transition metal catalyzed carbon-carbon bond forming reactions. Alkenes can also be epoxidized and the resulting epoxide can be opened with a nucleophile. Aromatic halides can be coupled to alkenes and alkynes by transition metal catalyzed carbon-carbon bond forming reactions.

The conversion of (24) to (25) can be accomplished by treating the former with a deprotecting agent in a solvent. Deprotecting agents include hydrogen and palladium, HCl, and TFA. Specific examples of solvents include MEOH, DCM, THF, and dioxane. The reaction generally proceeds at room temperature. The reaction time is generally about two hours to about 24 hours.

The conversion of (25) to (26) can be accomplished by treating the former with a nucleophilic solvent. Specific examples of nucleophilic solvents include MeOH and EtOH. The reaction generally proceeds at room temperature, but can be run at elevated temperatures. The reaction time is generally about 2 hours to about 60 hours.

Scheme 11

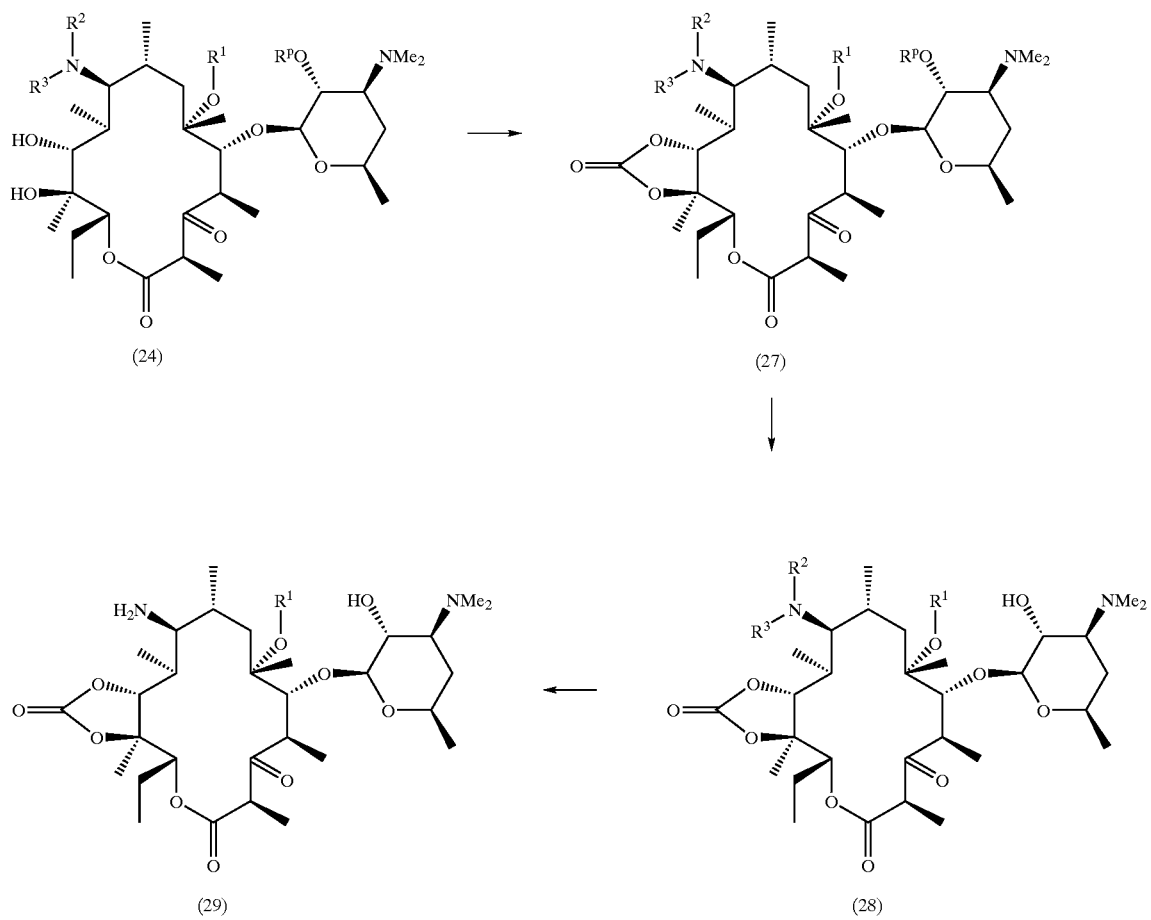

As shown in Scheme 11, the conversion of (24), wherein $R^1$, $R^2$, $R^3$, and $R^P$ are defined above, to (27) can be accomplished by treating the former with phosgene, triphosgene, or CDI and a base in a solvent. Specific examples of bases include pyridine, lutidine, LiHMDS, NaHMDS, KHMDS, DBU, TEA, and diisopropylethylamine. Specific examples of solvents include DCM, chloroform, THF, and dioxane. Although the reaction generally proceeds at −60° C., it can be run at elevated temperatures as needed. The reaction time is generally about 30 minutes to about 16 hours.

If $R^1$, $R^2$, or $R^3$ contain a double bond or a halide, the double bond or halide may be elaborated by means well known in the art. For example, alkenes and alkynes can be coupled to aromatic halides and triflates by transition metal catalyzed carbon-carbon bond forming reactions. Alkenes can also be epoxidized and the resulting epoxide can be opened with a nucleophile. Aromatic halides can be coupled to alkenes and alkynes by transition metal catalyzed carbon-carbon bond forming reactions.

The conversion of (27) to (28) can be accomplished by treating the former with nucleophilic solvent. Specific examples of nucleophilic solvents include MeOH and EtOH. Although the reaction temperature is generally room temperature, it can be run at elevated temperatures. The reaction time is generally about 2 hours to about 60 hours.

The conversion of (28) to (29) can be accomplished by treating the former with a deprotecting agent in a solvent. Specific examples of deprotecting agents include TFA and HCl in MeOH. Specific examples of solvents include MeOH, EtOH, THF, DCM, and dioxane. The reaction generally proceeds at room temperature, but can be run at elevated temperatures. The reaction time is generally about one hour to about 16 hours.

Scheme 12

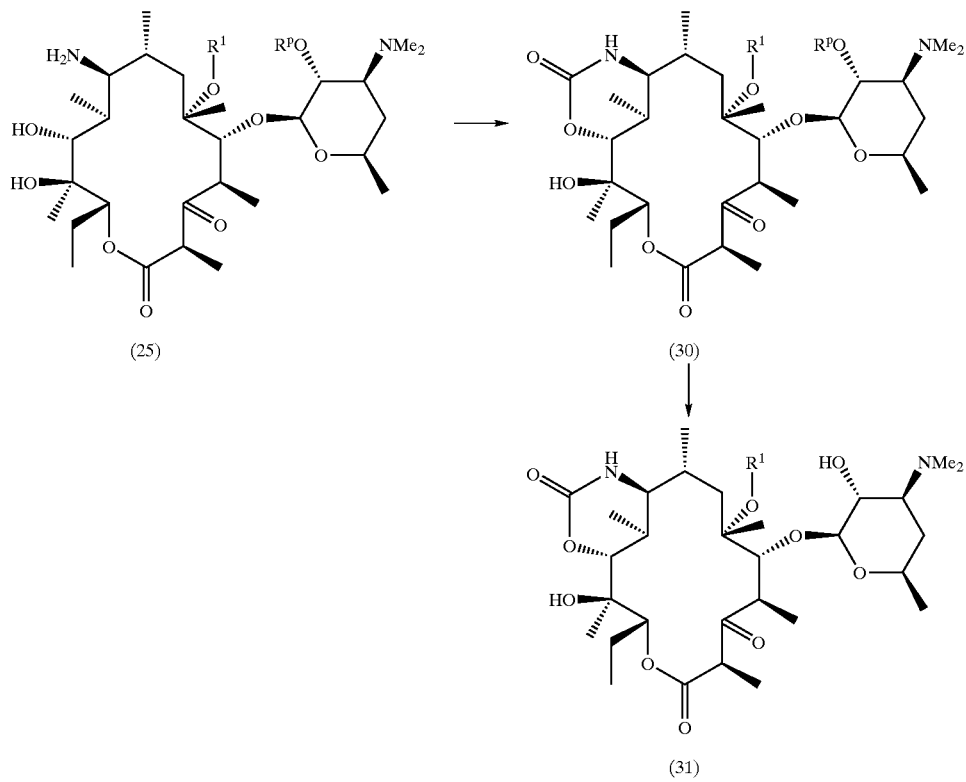

As shown in Scheme 12, the conversion of (25), wherein $R^1$ and $R^p$ are defined CDI and a base in a solvent. Specific examples of bases include pyridine, lutidine, DMAP, LiHMDS, NaHMDS, KHMDS, DBU, TEA, and diisopropylethylamine. Specific examples of solvents include DCM, chloroform, THF, and dioxane. Although the reaction generally proceeds at −60° C., it can be run at elevated temperatures as needed. The reaction time is generally about 30 minutes to about 16 hours.

The conversion of (30) to (31) can be accomplished by treating the former with a nucleophilic solvent. Specific examples of nucleophilic solvents include MeOH and EtOH. Although the reaction generally proceeds at elevated temperatures, it can be run at room temperature. The reaction time is generally about 2 hours to about 60 hours.

Scheme 13

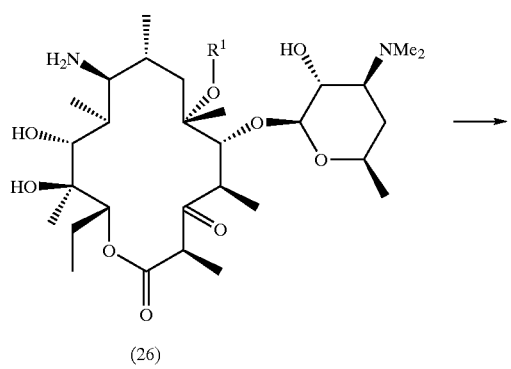

-continued

As shown in Scheme 13, the conversion of (26), wherein $R^1$ and $R^7$ are defined above, to (32) can be accomplished by treating the former with an aldehyde in a solvent. Specific examples of aldehydes include formaldehyde, acetaldehyde, phenylacetaldehyde, and acrolein. Specific examples of solvents include MeOH, EtOH, THF, and mixtures thereof. Although the reaction generally proceeds at room temperature, it can be run at lower or elevated temperatures, as needed. The reaction time is generally about three hours to about four days.

The present invention will now be described in connection with certain preferred embodiments, which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments and are presented to provide what is believed to be the most useful and readily understood description of its procedures and conceptual aspects.

EXAMPLE 1 compound of formula (I): $R^1$ is $CH_2CH=CH_2$; $R^2$ is hydrogen; $R^3$ is hydrogen; $R^4$ is hydrogen; $R^5$ is hydrogen; $R^6$ is hydrogen; $R^p$'s hydrogen

EXAMPLE 1A compound of formula (1) in Scheme 1: $R^6$ is Si$(CH_3)_3$; $R^p$ is $Si(CH_3)_3$ Example 1A was prepared as described in Examples 30–32 of U.S. Pat. No. 4,990,602.

EXAMPLE 1B compound of formula (2) in Scheme 1: $R^1$ is $CH_2=CHCH_2$

A solution of Example 1A (100.0 g, 96.9 mmol), allyl tert-butyl carbonate (18.38 g, 116.28 mmol), tris(dibenzylideneacetone)dipalladium(0) (0.48 g, 0.52 mmol), and dppb (0.44 g, 1.40 mmol) in toluene (600 mL) was heated to 80° C. for three hours, cooled to room temperature, washed with 5% $Na_2CO_3$ and brine, and concentrated. The concentrate was suspended in acetonitrile (900 mL) and water (100 mL), treated with acetic acid (250 mL), stirred for 6 days, diluted with ethyl acetate (600 mL), washed with 5% $Na_2CO_3$ and brine, dried ($MgSO_4$), filtered, and concentrated. The concentrate was purified by flash column chromatography on silica gel with 100:10:1 dichloromethane/methanol/concentrated ammonium hydroxide to provide the desired product.

EXAMPLE 1C compound of formula (I): $R^1$ is $CH_2=CHCH_2$; $R^2$ is hydrogen; $R^3$ is hydrogen; $R^4$ is hydrogen; $R^5$ is hydrogen; $R^6$ is hydrogen; $R^p$ is hydrogen A mixture of Example 1B (4.5 g, 5.8 mmol), ammonium acetate (22.8 g, 293 mmol) and sodium cyanoborohydride (1.7 g, 27.1 mmol) in methanol (100 mL) at room temperature was treated with a solution of 30% titanium(III) chloride in 2N HCl (5.1 mL) over 1 hour, stirred for 24 hours, diluted with water, and extracted with ethyl acetate. The aqueous phase was adjusted to pH 7 with 2N NaOH, extracted with ethyl acetate, dried ($MgSO_4$), filtered, and concentrated. The concentrate was purified by flash column chromatography on silica gel with 100:5:1 dichloromethane/methanol/concentrated ammonium hydroxide to provide the desired product. MS (ESI) m/z 775 (M+H)$^+$, 797 (M+Na)$^+$; $^1$H NMR (CDCl$_3$) δ6.02 (m, 1H), 5.40 (dd, J=1.4, 17.3 Hz, 1H), 5.22 (dd, J=1.02, 10.54 Hz, 1H), 4.93 (dd, J=2.04, 13.23 Hz, 1H), 4.90 (d, J=4.41 Hz, 1H), 4.40 (d, J=7.12 Hz, 1H), 4.10–4.00 (m, 2H), 3.81 (d, J=7.46 Hz, 1H), 3.77 (d, J=9.84 Hz, 1H), 3.64 (br s, 1H), 3.49 (m, 1H), 3.32 (s, 3H), 3.17 (dd, J=7.12, 10.17 Hz, 1H), 3.10–2.90 (m, 2H), 2.66 (dd, J=1.02, 5.54 Hz, 1H), 2.28 (s, 6H), 1.51 (s, 3H), 1.32 (d, J=6.44 Hz, 3H), 1.25 (s, 3H), 1.21 (d, J=9.5 Hz, 3H), 1.24 (d, J=7.12 Hz, 3H), 1.22 (d, J=6.78 Hz, 3H), 1.18 (d, J=7.12 Hz, 3H), 1.15 (d, J=7.12 Hz, 3H), 1.12 (s, 3H), 1.05 (d, 6.78 Hz, 3H), 0.85 (t, J=7.46 Hz, 3H); $^{13}$C NMR (CDCl$_3$) δ176.1, 135.7, 117.4, 104.0, 98.5, 81.4, 80.8, 80.0, 78.9, 78.1, 75.9, 74.0, 73.7, 71.0, 68.9, 66.5, 65.4, 65.0, 64.7, 49.8, 46.6, 40.5, 40.5, 40.2, 37.6, 36.1, 34.5, 32.1, 31.8, 24.1, 22.4, 22.1, 21.7, 21.4, 19.0, 17.2, 16.8, 15.3, 11.0, 10.7.

EXAMPLE 2 compound of formula (I): $R^1$ is hydrogen; $R^2$ is hydrogen; $R^3$ is hydrogen; $R^4$ and $R^5$ together are —C(O)—; $R^6$ is hydrogen; $R^p$ is hydrogen

EXAMPLE 2A

9(S)-erythromycylamine

9(S)-Erythromycylamine was prepared as described in *J. Med. Chem.*, 17(1), 105-107 (1974).

EXAMPLE 2B compound of formula (6) in Scheme 3: $R^2$ is $C_6H_5CH_2OC(O)$; $R^3$ is hydrogen; $R^p$ is $C(O)CH_3$ Example 2A (70.0 g, 95.0 mmol) in dioxane (400 mL) at room temperature was treated with N-(benzyloxycarbonyloxy)succinimide (25.0 g, 100 mmol), stirred for 3 hours, treated with acetic anhydride (15 mL, 135 mmol), stirred for 16 hours, and concentrated to provide of the desired product. MS (ESI) m/z 911 (M+H)$^+$.

EXAMPLE 2C compound of formula (7) in Scheme 3: $R^2$ is $C_6H_5CH_2OC(O)$; $R^3$ is hydrogen; $R^p$ is $C(O)CH_3$ A solution of pyridine (5.08 g, 64 mmol) and triphosgene (593 mg, 2.00 mmol) in dichloromethane (30 mL) at −70° C. was treated with a solution of Example 2B (1.3 g, 1.43 mmol) in dichloromethane (20 mL), stirred at room temperature for three hours, treated with 5% $Na_2CO_3$, washed with brine, dried ($Na_2SO_4$), filtered, and concentrated. The concentrate was purified by flash column chromatography on silica gel with 97.75:2:0.25 dichloromethane/methanol/concentrated ammonium hydroxide to provide of the desired product. MS (ESI) m/z 937 (M+H)$^+$.

EXAMPLE 2D compound of formula (I): $R^1$ is hydrogen; $R^2$ is hydrogen; $R^3$ is hydrogen; $R^4$ and $R^5$ together are —C(O)—; $R^6$ is hydrogen; $R^p$ is hydrogen A suspension of Example 2C (135 mg, 0.144 mmol) and 10% palladium on carbon (60 mg) in methanol (5 mL) at room temperature was stirred under hydrogen (1 atm) for 30 minutes, filtered through diatomaceous earth (Celite®), stirred for 12 hours, and concentrated. The concentrate was purified by flash column chromatography on silica gel with 94:5:1 dichloromethane/methanol/concentrated ammonium hydroxide to provide the desired product. MS (ESI) m/z 761 (M+H)$^+$.

EXAMPLE 3 compound of formula (I): $R^1$ and $R^2$ together are —C(O)—; $R^3$ is hydrogen; $R^4$ and $R^5$ together are —C(O)— and $R^6$ is $C(O)CH_3$; $R^p$ is hydrogen

EXAMPLE 3A compound of formula (9) in Scheme 4: $R^2$ is benzyloxycarbonyl; $R^3$ is hydrogen; $R^6$ is $C(O)CH_3$; $R^p$ is $C(O)CH_3$ A solution of Example 2B (5.43 g, 5.96 mmol), acetic anhydride (1.22 g, 11.92 mmol), and triethylamine (1.20 g, 11.92 mmol) in dichloromethane (20 mL) at room temperature was treated with 4-dimethylaminopyridine (436 mg, 3.57 mmol), stirred for 16 hours, treated with 5% aqueous $Na_2CO_3$, washed with brine, dried ($Na_2SO_4$), filtered, and concentrated. The concentrate was purified by flash column chromatography on silica gel with 97.5:2:0.5 dichloromethane/methanol/concentrated ammonium hydroxide to provide of the desired product. MS (ESI) m/z 953 (M+H)$^+$.

EXAMPLE 3B compound of formula (10) in Scheme 4: $R^2$ is benzyloxycarbonyl; $R^3$ is hydrogen; $R^6$ is C(O)CH$_3$; $R^p$ is C(O)CH$_3$ The desired product was prepared by substituting Example 3A (3.1 g, 3.25 mmol) for Example 2B in Example 2C to provide the desired product. MS (ESI) m/z 979 (M+H)$^+$.

EXAMPLE 3C compound of formula (11) in Scheme 4: $R^6$ is C(O)CH$_3$; $R^p$ is C(O)CH$_3$ A suspension of Example 3B (5.0 g, 5.1 mmol) and 10% palladium on carbon (1.0 g) in ethanol (50 mL) at room temperature was stirred under hydrogen (1 atm) for 30 minutes, filtered through diatomaceous earth (Celite®), and concentrated. The concentrate was purified by flash column chromatography on silica gel with 94:5:1 dichloromethane/methanol/concentrated ammonium hydroxide to provide the desired product. MS (ESI) m/z 845 (M+H)$^+$.

EXAMPLE 3D compound of formula (12) in Scheme 5: $R^6$ is C(O)CH$_3$; $R^p$ is C(O)CH$_3$ A solution of Example 3C (845 mg, 1.00 mmol) and cabonylidiimidazole (811 mg, 5.00 mmol) in THF (15 mL) at room temperature was treated with sodium hydride (120 mg, 5.00 mmol), stirred for 30 minutes, heated to reflux for one hour, cooled to room temperature, diluted with ethyl acetate, washed with 5% $Na_2CO_3$ and brine, dried ($Na_2SO_4$), filtered, and concentrated. The concentrate was purified by flash column chromatography on silica gel with 2:1 hexanes/acetone to provide of the desired product. MS (ESI) m/z 871 (M+H)$^+$.

EXAMPLE 3E compound of formula (I): $R^1$ and $R^2$ together are —C(O)—; $R^3$ is hydrogen; $R^4$ and $R^5$ together are —C(O)—; and $R^6$ is C(O)CH$_3$; $R^p$ is hydrogen A solution of Example 3D (38 mg, 0.044 mmol) in methanol (5 mL) at room temperature was stirred for 16 hours and concentrated. The concentrate was purified by flash column chromatography on silica gel with 97.75:2.0:0.25 dichloromethane/methanol/concentrated ammonium hydroxide to provide of the desired product. MS (ESI) m/z 829 (M+H)$^+$.

EXAMPLE 4 compound of formula (I): $R^1$ is hydrogen; $R^2$ is $C_6H_5CH_2CH_2CH_2$; $R^3$ is hydrogen; $R^4$ and $R^5$ together are —C(O)—; $R^6$ is hydrogen; $R^p$ is hydrogen A solution of acetic acid (16 mL, 0.16 mmol) and Example 2D (76 mg, 0.10 mmol) in methanol (5 mL) at room temperature was treated with hydrocinnamaldehyde (70 mg, 0.5 mmol) and magnesium sulfate (50 mg, 0.42 mmol), stirred for 2 hours, treated with sodium cyanoborohydride (100 mg, 1.60 mmol), stirred for 3 hours, diluted with ethyl acetate, washed with 5% $Na_2CO_3$ and brine, dried ($Na_2SO_4$), filtered, and concentrated. The concentrate was purified by flash column chromatography on silica gel with 94:5:1 dichloromethane/methanol/concentrated ammonium hydroxide to provide of the desired product. MS (ESI) m/z 879 (M+H)$^+$.

EXAMPLE 5 compound of formula (I): $R^1$ is (quinolin-3-yl)CH=CHCH$_2$; $R^2$ is C(CH$_3$)$_3$OC(O); $R^3$ is hydrogen; $R^4$ is hydrogen; $R^5$ is hydrogen; $R^6$ is C(O)CH$_3$; $R^p$ is hydrogen

EXAMPLE 5A compound of formula (15) of Scheme 7: $R^1$ is CH$_2$=CHCH$_2$; $R^2$ is C(CH$_3$)$_3$OC(O); $R^3$ is hydrogen Example 1C (2.33 g, 3.0 mmol) in 1,4-dioxane (50 mL) at room temperature was treated with a solution of di-tert-butyl dicarbonate (0.98 g, 4.5 mmol) in 1,4-dioxane (10 mL) over 10 minutes, stirred for 48 hours, and concentrated. The concentrate was dissolved in ethyl acetate, washed with 5% $Na_2CO_3$ and brine, dried ($Na_2SO_4$), filtered, and concentrated. The concentrate was purified by flash column chromatography on silica gel with 100:2:0.2 dichloromethane/methanol/concentrated ammonium hydroxide to provide of the desired product. MS (ESI(+)) m/z 875 (M+H)$^+$; 897 (M+Na)$^+$; $^1$H NMR (CDCl$_3$) δ6.02 (m, 1H), 5.85 (m, 1H), 5.40 (dd, J=1.4, 17.3 Hz, 1H), 5.16 (dd, J=1.8, 10.9 Hz, 1H), 4.83 (d, J=4.41 Hz, 1H), 4.66 (br d, J=10.5 Hz, 1H), 4.33 (d, J=7.12 Hz, 1H), 4.29–3.40 (m, 7H), 3.30 (s, 3H), 3.18 (dd, J=7.42, 10.5 Hz, 1H), 3.10–2.90 (m, 2H), 2.29 (s, 6H), 1.49 (s, 3H), 1.43 (s, 9H), 1.33 (d, J=6.10 Hz, 3H), 1.24 (s, 3H), 1.21 (d, J=6.77 Hz, 3H), 1.19 (d, J=6.43 Hz, 3H), 1.17 (d, J=6.78 Hz, 3H), 1.12 (s, 3H), 1.07 (d, J=6.78 Hz, 3H), 0.99 (d, 7.11 Hz, 3H), 0.86 (t, J=7.46 Hz, 3H); $^{13}$C NMR (CDCl$_3$) δ175.7, 156.3, 135.0, 114.7, 103.1, 97.2, 81.0, 79.4, 78.4, 78.0, 77.8, 77.7, 75.2, 72.2, 70.5, 70.2, 68.9, 65.4, 65.4, 63.2, 60.1, 49.2, 45.6, 40.1, 40.1, 39.6, 37.3, 35.3, 32.7, 32.2, 28.5, 28.4, 28.4, 28.4, 24.6, 21.6, 21.4, 21.0, 19.6, 18.5, 15.9, 15.8, 13.6, 10.9, 9.55.

EXAMPLE 5B compound of formula (16) of Scheme 7: $R^1$ is CH$_2$=CHCH$_2$; $R^2$ is C(CH$_3$)$_3$OC(O); $R^3$ is hydrogen; $R^6$ is C(O)CH$_3$; $R^p$ is C(O)CH$_3$ A solution of Example 5A (1.5 g, 1.7 mmol) and triethylamine (0.610 mL, 4.40 mmol) in dichloromethane (20 mL) at room temperature was treated slowly with acetic anhydride (0.4 mL, 4.21 mmol), stirred for 24 hours, washed with 5% $Na_2CO_3$ and brine, dried ($Na_2SO_4$), filtered, and concentrated. The concentrate was purified by flash column chromatography on silica gel with 100:2:0.2 dichloromethane/methanol/concentrated ammonium hydroxide to provide the desired product. MS (ESI(+)) m/z 959 (M+H)$^+$, 981 (M+Na)$^+$; $^1$H NMR (CDCl$_3$) δ5.95 (m, 2H), 5.40 (dd, J=1.4, 17.3 Hz, 1H), 5.16 (dd, J=1.8, 10.9 Hz, 1H), 4.87 (d, J=4.41 Hz, 1H), 4.65–4.75 (m, 3H), 4.51 (d, J=7.46 Hz, 1H), 4.35 (dd, 1H), 4.24 (dd, 1H), 4.05 (m, 1H), 3.96 (d, J=9.84, 1H), 3.70–3.50 (m, 3H), 3.32 (s, 3H), 2.27

(s, 6H), 2.15 (s, 3H), 2.00 (s, 3H), 1.40 (d, J=6.81 Hz, 3H), 1.43 (s, 9H), 1.33 (d, J=6.10 Hz, 3H), 1.20 (s, 3H), 1.17 (d, J=6.77 Hz, 3H), 1.13 (s, 3H), 1.09 (d, J=6.80 Hz, 3H), 1.07 (s, 3H), 1.06 (d, J=7.70 Hz, 3H), 0.98 (d, 6.44 Hz, 3H), 0.86 (t, J=7.46 Hz, 3H).

EXAMPLE 5C compound of formula (16) of Scheme 7: $R^1$ is (quinolin-3-yl)CH=CHCH$_2$; $R^2$ is C(CH$_3$)$_3$OC(O); $R^3$ is hydrogen; $R^6$ is C(O)CH$_3$; $R^p$ is C(O)CH$_3$ A mixture of Example 5B (317 mg, 0.33 mmol), 3-bromoquinoline (128 mg, 0.62 mmol), tetrabutylammonium bromide (151 mg, 0.47 mmol), N,N-diisopropylethylamine (151 mg, 1.17 mmol), palladium(II) acetate (6.6 mg, 0.03 mmol) and DME (6 mL) in a sealed tube was stirred at 80° C. for 20 hours, cooled to room temperature, diluted with ethyl acetate, washed with 5% Na$_2$CO$_3$ and brine, dried (MgSO$_4$), filtered, and concentrated to provide the desired product.

EXAMPLE 5D compound of formula (I): $R^1$ is (quinolin-3-yl)CH=CHCH$_2$; $R^2$ is C(CH$_3$)$_3$OC(O); $R^3$ is hydrogen; $R^4$ is hydrogen; $R^5$ is hydrogen; $R^6$ is C(O)CH$_3$; $R^p$ is hydrogen A solution of Example 5C in methanol (20 mL) at room temperature was stirred for 30 hours and concentrated. The concentrate was purified by flash column chromatography on silica gel with 100:10:1 dichloromethane/methanol/concentrated ammonium hydroxide to provide of the desired product. MS (ESI(+)) m/z 1044 (M+H)$^+$; HRMS (ESI(+)) calcd for C$_{56}$H$_{90}$N$_3$O$_{15}$: 1044.6366. Found 1044.6356.

EXAMPLE 6 compound of formula (II): $R^1$ is (quinolin-3-yl)CH=CHCH$_2$; $R^2$ is methoxy; $R^3$ is hydrogen; $R^4$ is hydrogen; $R^5$ is hydrogen; $R^p$ is hydrogen

EXAMPLE 6A compound of formula (18) in Scheme 8: $R^1$ is (quinolin-3-yl)CH=CHCH$_2$; $R^p$ is C$_6$H$_5$C(O)

Example 6A was prepared as described in Example 18 of U.S. Pat. No. 5,866,549.

EXAMPLE 6B compound of formula (19) in Scheme 8: $R^1$ is (quinolin-3-yl)CH=CHCH$_2$; $R^p$ is methoxy; $R^p$ is C$_6$H$_5$C(O)

Example 6A (4.22 g, 5.00 mmol), O-methylhydroxylamine hydrochloride (0.640 g, 8 mmol), and p-toluenesulfonic acid (65 mg, 0.34 mmol) in ethanol (50 mL) were heated to 70° C. for 5 days, cooled to room temperature, diluted with dichloromethane, washed with 5% Na$_2$CO$_3$ and brine, dried (Na$_2$SO$_4$), filtered, and concentrated. The concentrate was purified by flash column chromatography on silica gel with 1:1 hexanes/acetone to provide the desired product. MS (ESI) m/z 876 (M+H)$^+$.

EXAMPLE 6C compound of formula (II): $R^1$ is (quinolin-3-yl)CH=CHCH$_2$; $R^2$ is methoxy; $R^3$ is hydrogen; $R^4$ is hydrogen; $R^5$ is hydrogen; $R^p$ is hydrogen A solution of Example 6B (100 mg, 0.113 mmol) and molybdenum(VI) oxide (30 mg, 0.1 mmol) in methanol (2 mL) at 0° C. was treated with sodium cyanoborohydride (300 mg, 4.8 mmol), warmed to room temperature, stirred for 24 hours, diluted with ethyl acetate, washed with 5% Na$_2$CO$_3$ and brine, dried (Na$_2$SO$_4$), filtered, and concentrated. The concentrate was purified by flash column chromatography on silica gel with 94.5:5:0.5 dichloromethane/methanol/concentrated ammonium hydroxide to provide the desired product. MS (ESI) m/z 772 (M+H)$^+$.

EXAMPLE 7 compound of formula (II): $R^1$ is (quinolin-3-yl)CH=CHCH$_2$; $R^2$ is hydrogen; $R^3$ is hydrogen; $R^4$ is hydrogen; $R^5$ is hydrogen; $R^p$ is hydrogen

EXAMPLE 7A compound of formula (21) in Scheme 9: $R^1$ is CH$_2$=CHCH$_2$

Example 1C (2.1 g, 2.7 mmol) in methanol (20 mL) at 0° C. was slowly treated with 1N HCl (20 mL) over 10 minutes, warmed to room temperature, stirred for 24 hours, adjusted to pH 11 with 2N NaOH, and extracted with ethyl acetate. The extract was dried (NaSO$_4$), filtered, and concentrated. The concentrate was purified by flash column chromatography on silica gel with 100:5:1 dichloromethane/methanol/concentrated ammonium hydroxide to provide desired product. $^1$H NMR (CDCl$_3$) δ5.88 (m, 1H), 5.28 (dd, J=1.7, 17.3 Hz, 1H), 5.12 (dd, J=1.35, 10.51 Hz, 1H), 5.01 (dd, J=2.04, 11.19 Hz, 1H), 4.63 (d, J=7.46 Hz, 1H), 3.80–4.05 (m, 3H), 3.50 (m, 1H), 3.22 (dd, J=7.8, 10.5 Hz, 1H), 2.73 (m, 1H), 2.45 (m, 2H), 2.24 (s, 6H), 1.39 (s, 3H), 1.29 (d, J=6.42 Hz, 3H), 1.20 (d, J=6.11 Hz, 3H), 1.19 (d, J=7.12 Hz, 3H), 1.15 (d, J=6.78 Hz, 3H), 1.13 (d, J=6.78 Hz, 3H), 1.06 (s, 3H), 0.86 (t, J=7.12 Hz, 3H); $^{13}$C NMR (CDCl$_3$) δ176.1, 134.4, 115.1, 105.6, 81.6, 78.5, 77.3, 74.2, 70.3, 69.5, 69.1, 69.0, 65.2, 64.5, 61.5, 43.8, 40.2, 40.2, 37.4, 35.0, 32.0, 31.5, 27.8, 21.2, 21.1, 21.0, 17.1, 15.7, 15.7, 13.5, 10.6, 7.6.

EXAMPLE 7B compound of formula (22) in Scheme 9: $R^1$ is CH$_2$=CHCH$_2$; $R^2$ is C(CH$_3$)$_3$OC(O); $R^3$ is hydrogen A solution of Example 7A (992 mg, 1.6 mmol) in 1,4-dioxane (15 mL) at room temperature was treated with a solution of di-tert-butyl dicarbonate (420 mg, 1.92 mmol) in 1,4-dioxane (10 mL) over 10 minutes, stirred for 24 hours, and concentrated. The concentrate was dissolved in ethyl acetate, washed with 5% Na$_2$CO$_3$ and brine, dried (Na$_2$SO$_4$), filtered, and concentrated. The concentrate was purified by flash column chromatography on silica gel with 100:2:0.2 dichloromethane/methanol/concentrated ammonium hydroxide to provide the desired product. MS (ESI(+)) m/z 717 (M+H)$^+$; 739 (M+Na)$^+$; $^1$H NMR (CDCl$_3$) δ5.85 (m, 1H), 5.82 (d, J=9.0 Hz, 1H), 5.23 (dd, J=1.7, 17.29 Hz, 1H), 5.05 (dd, J=1.35, 10.50 Hz, 1H), 4.68 (d, J=7.8 Hz, 1H), 4.45 (d, J=9.0 Hz, 1H), 4.33 (d, J=5.74 Hz, 1H), 3.98 (s, 1H), 3.88 (m, 1H), 3.80 (d, J=9.9 Hz, 1H), 3.49 (m, 1H), 3.30 (d, J=4.0 Hz, 1H), 3.22 (dd, J=7.8, 10.98 Hz, 1H), 2.76 (m, 1H), 2.45 (m, 2H), 2.25 (s, 6H), 1.43 (s, 9H), 1.33 (s, 3H), 1.30 (d, J=6.8 Hz, 3H), 1.20 (d, J=6.11 Hz, 3H), 1.18 (d, J=6.8 Hz, 3H), 1.15 (d, J=6.78 Hz, 3H), 1.07(d, J=7.12 Hz, 3H), 1.04 (s, 3H), 0.91 (t, J=7.12 Hz, 3H); $^{13}$C NMR (CDCl$_3$) δ178.4, 156.2, 134.8, 114.2, 105.3, 89.6, 81.6, 79.2, 79.1, 77.9, 74.8, 70.3, 69.1, 68.8, 65.1, 62.3, 61.3, 43.8, 40.1, 40.1, 37.6, 36.6, 32.6, 31.2, 28.4, 28.4, 28.4, 27.9, 21.1, 21.0, 20.8, 16.1, 15.5, 15.4, 12.0, 11.1, 7.2.

EXAMPLE 7C compound of formula (23) in Scheme 9: $R^1$ is $CH_2=CHCH_2$; $R^2$ is $C(CH_3)_3OC(O)$; $R^3$ is hydrogen; $R^p$ is $CH_3C(O)$ A solution of Example 7B (990 mg, 1.38 mmol) and triethylamine (0.66 mL, 4.76 mmol) in dichloromethane (10 mL) at room temperature was treated slowly with acetic anhydride (0.25 mL, 2.07 mmol), stirred for 24 hours, washed with 5% $Na_2CO_3$ and brine, dried ($Na_2SO_4$), filtered, and concentrated. The concentrate was purified by flash column chromatography on silica gel with 100:5:0.5 dichloromethane/methanol/concentrated ammonium hydroxide to provide the desired product. MS (ESI(+)) m/z 759 (M+H)$^+$; 781 (M+Na)$^+$; $^1$H NMR (CDCl$_3$) δ5.87 (m, 2H), 5.27 (dd, J=1.36, 17.3 Hz, 1H), 5.05 (dd, J=1.36, 11.8 Hz, 1H), 4.97 (d, J=8.33 Hz, 1H), 4.63 (dd, J=8.13, 10.2 Hz, 1H), 4.50 (d, J=10.2 Hz, 1H), 4.01 (br s, 1H), 3.92 (m, 2H), 3.70 (d, J=9.84 Hz, 1H), 3.51 (m, 1H), 3.35 (m, 1H), 3.20 (m, 1H), 2.75–2.60 (m, 2H), 2.24 (s, 6H), 2.10 (s, 3H), 1.43 (s, 9H), 1.36 (s, 3H), 1.28 (d, J=6.8 Hz, 3H), 1.21 (d, J=6.10 Hz, 3H), 1.18 (d, J=6.0 Hz, 3H), 1.09 (d, J=6.78 Hz, 3H), 1.06 (d, J=7.8 Hz, 3H), 1.05 (s, 3H), 0.89 (t, J=7.12 Hz, 3H); $^{13}$C NMR (CDCl$_3$) δ177.8, 169.7, 156.1, 135.0, 115.2, 102.4, 80.9, 78.6, 78.5, 78.2, 74.8, 71.5, 69.4, 68.3, 63.5, 61.8, 61.5, 43.7, 40.1, 40.1, 36.9, 36.4, 31.4, 29.4, 28.3, 28.3, 28.3, 21.4, 21.3, 20.8, 20.7, 20.6, 15.6, 14.9, 12.7, 11.3, 7.4.

EXAMPLE 7D compound of formula (24) in Scheme 10: $R^1$ is $CH_2=CHCH_2$; $R^2$ is $C(CH_3)_3OC(O)$; $R^3$ is hydrogen; $R^p$ is $CH_3C(O)$ A solution of Example 7C (400 mg, 0.53 mmol) in dichloromethane (15 mL) at room temperature was treated with DMSO (1.17 mL) and EDCI (800 mg, 4.17 mmol), stirred for 1 hour, treated with pyridinium trifluoroacetate (800 mg, 4.17 mmol), stirred for 16 hours, washed with saturated NaHCO$_3$ and brine, dried (Na$_2$SO$_4$), filtered, and concentrated. The concentrate was purified by flash column chromatography on silica gel with 3:1 to 2:1 hexanes/acetone to provide the desired product. MS (ESI(+)) m/z 757 (M+H)$^+$; 779 (M+Na)$^+$; $^1$H NMR (CDCl$_3$) δ5.80 (m, 2H), 5.20 (dd, J=1.36, 17.0 Hz, 1H), 5.07 (dd, J=1.70, 10.5 Hz, 1H), 4.80 (d, J=10.9 Hz, 1H), 4.7 (dd, J=7.7, 10.5 Hz, 1H), 4.42 (d, J=7.5 Hz, 1H), 4.40-4.35 (m, 1H), 3.90 (m, 1H), 4.00–3.20 (m, 7H), 2.25 (s, 6H), 2.03 (s, 3H), 1.43 (s, 9H), 1.36 (s, 3H), 1.31 (d, J=6.7 Hz, 3H), 1.27 (d, J=7.17 Hz, 3H), 1.25 (d, J=6.1 Hz, 3H), 1.13 (s, 3H), 1.07 (d, J=6.8 Hz, 3H), 1.00 (d, J=6.44 Hz, 3H), 0.89 (t, J=7.4 Hz, 3H); $^{13}$C NMR (CDCl$_3$) δ203.5, 172.0, 169.9, 156.7, 134.9, 115.7, 101.3, 78.9, 78.4, 78.3, 74.8, 71.4, 69.4, 68.7, 63.9, 63.1, 61.0, 50.1, 45.9, 40.4, 40.4, 36.9, 36.4, 32.6, 31.4, 30.5, 28.4, 28.4, 28.4, 22.1, 21.4, 21.3, 20.9, 19.5, 16.1, 14.6, 13.4, 12.4, 11.1.

EXAMPLE 7E compound of formula (24) in Scheme 10: $R^1$ is (quinolin-3-yl)C=CHCH$_2$; $R^2$ is C(CH$_3$)$_3$OC(O); $R^3$ is hydrogen; $R^p$ is CH$_3$C(O)

Example 7D (430 mg, 0.57 mmol), 3-bromoquinoline (236 mg, 1.14 mmol), palladium(II) acetate (45 mg, 0.2 mmol), tetrabutylammonium bromide (219 mg, 0.68 mmol), and diisopropylethylamine (219 mg, 1.7 mmol) in DME (4 mL) in a sealed tube was heated to 100° C., stirred for 14 hours, cooled to room temperature, diluted with ethyl acetate, washed with 5% Na$_2$CO$_3$ and brine, dried (MgSO$_4$), filtered, and concentrated. The concentrate was purified by flash column chromatography on silica gel with 100:1:0.25 dichloromethane/methanol/concentrated ammonium hydroxide to provide the desired product. MS (ESI(+)) m/z 885 (M+H)$^+$.

EXAMPLE 7F compound of formula (25) in Scheme 10: $R^1$ is (quinolin-3-yl)CH=CHCH$_2$; $R^p$ is CH$_3$C(O)

Example 7E (100 mg, 0.11 mmol) in dichloromethane (20 mL) at room temperature was treated with trifluoroacetic acid (2 mL), stirred for two hours, and concentrated. The concentrate was purified by flash column chromatography on silica gel with 100:2:0.1 dichloromethane/methanol/concentrated ammonium hydroxide to provide the desired product.

EXAMPLE 7G compound of formula (II): $R^1$ is (quinolin-3-yl)CH=CHCH$_2$; $R^2$ is hydrogen; $R^3$ is hydrogen; $R^4$ is hydrogen; $R^5$ is hydrogen; $R^p$ is hydrogen A solution of Example 7F in methanol (10 mL) at room temperature was stirred for 16 hours and concentrated. The concentrate was purified by flash column chromatography on silica gel with 100:2:0.1 dichloromethane/methanol/concentrated ammonium hydroxide to provide the desired product. MS (ESI(+)) m/z 742 (M+H)$^+$; 764 (M+Na)$^+$; $^1$H NMR (CDCl$_3$) δ9.03 (d, J=2.04 Hz, 1H), 8.15 (d, J=2.04 Hz, 1H), 8.06 (dd, J=1.00, 8.14 Hz, 1H), 7.80 (dd, J=1.36, 8.14 Hz, 1H), 7.65 (ddd, J=1.36, 8.14 and 8.14 Hz, 1H), 7.51 (ddd, J=1.00, 8.14 and 8.14 Hz, 1H), 6.64 (d, J=17.27 Hz, 1H), 6.48 (dt, J=5.40, 17.27 Hz, 1H), 5.24 (dd, J=1.71, 10.17 Hz, 1H), 4.59 (d, J=6.41 Hz, 1H), 4.33 (d, J=7.47 Hz, 1H), 4.06 (m, 1H), 3.87 (q, J=6.79 Hz, 1H), 3.76 (br s, 1H), 3.55 (m, 1H), 3.27 (dd, 1H), 3.20 (m, 1H), 2.28 (s, 1H), 1.49 (s, 1H), 1.43 (d, J=7.8 Hz, 3H), 1.28 (d, J=6.78 Hz, 3H), 1.25 (d, J=6.1 Hz, 3H), 1.20 (d, J=6.8 Hz, 3H), 1.19 (s, 3H), 1.09(d, J=6.45 Hz, 3H), 0.89 (t, J=7.46 Hz, 3H); $^{13}$C NMR (CDCl$_3$) δ204.3, 168.9, 149.1, 146.7, 131.9, 129.6, 128.6, 128.6, 128.5, 127.5, 127.3, 127.2, 126.1, 103.6, 78.9, 78.8, 77.9, 73.7, 70.1, 69.7, 69.3, 65.4, 63.7, 62.7, 50.1, 45.9, 40.1, 40.1, 36.5, 32.5, 30.9, 28.4, 22.13, 21.9, 21.2, 20.4, 16.0, 14.6, 14.2, 12.8, 10.9.

EXAMPLE 8 compound of formula (II): $R^1$ is (quinolin-3-yl)CH=CHCH$_2$; $R^2$ is hydrogen; $R^3$ and $R^4$ together are —C(O)—; $R^5$ is hydrogen; $R^p$ is hydrogen

EXAMPLE 8A compound of formula (30) in Scheme 12: $R^1$ is (quinolin-3-yl)CH=CHCH$_2$; $R^p$ is CH$_3$C(O)

N,N-diisopropylethylamine (1.33 mL, 7.6 mmol), DMAP (6.9 mg, 0.057 mmol and Example 7F (150 mg, 0.17 mmol) in dichloromethane (3 mL) at −10° C. was treated with triphosgene (75 mg, 0.26 mmol), stirred for 10 minutes, warmed to room temperature, stirred for two hours, washed with 5% Na$_2$CO$_3$ and brine, dried (MgSO$_4$), filtered, and concentrated to provide the desired product.

EXAMPLE 8B compound of formula (II): $R^1$ is (quinolin-3-yl)CH=CHCH$_2$; $R^2$ is hydrogen; $R^3$ and $R^4$ together are —C(O)—; $R^5$ is hydrogen; $R^p$ is hydrogen Example 8A in methanol (20 mL) was heated to 50° C., stirred for five hours, and concentrated. The concentrate was purified by flash column chromatography on silica gel with 100:2:0.5 dichloromethane/methanol/concentrated ammonium hydroxide to provide the desired product. MS (ESI(+)) m/z 768 (M+H)$^+$; 790 (M+Na)$^+$; $^1$H NMR (CDCl$_3$) δ9.13 (d, J=1.17 Hz, 1H), 8.11 (d, J=1.7 Hz, 1H), 8.04 (br d, J=8.13 Hz, 1H), 7.78 (dd, J=1.02 and 8.13 Hz, 1H), 7.65 (ddd, J=1.02, 8.13 and 8.13 Hz, 1H), 7.51 (ddd, J=1.02, 8.13 and 8.13 Hz, 1H), 6.67 (d, J=16.27 Hz, 1H), 6.43 (d, J=5.43, 16.27 Hz, 1H), 6.18 (br s, 1H), 5.24 (dd, J=3.05, 9.17 Hz, 1H), 4.53 (d, J=4.41 Hz, 1H), 4.43 (d, J=7.46 Hz, 1H), 4.26 (d, J=1.36 Hz, 1H), 4.22 (m, 1H), 4.03 (dd, J=5.79 and 17.2 Hz, 1H), 3.87 (q, J=6.79 Hz, 1H), 3.55 (m, 2H), 3.27 (dd, J=7.46, 10.18 Hz, 1H), 2.95 (m, 1H), 2.84 (m, 1), 2.28 (s, 6H), 1.41 (s, 3H), 1.38 (d, J=6.78 Hz, 3H), 1.31 (d, J=6.78 Hz, 3H), 1.26 (s, 3H), 1.18 (d, J=5.77 Hz, 3H), 1.16 (d, J=6.10 Hz, 3H), 1.09 (d, J=6.77 Hz, 3H), 0.85 (t, J=7.46 Hz, 3H); $^{13}$C NMR (CDCl$_3$) δ204.7, 168.6, 153.3, 149.2, 146.5, 131.7, 129.6, 128.8, 128.6, 128.4, 127.6, 127.4, 126.5, 126.1, 102.9, 78.8, 77.5, 77.1, 75.7, 73.4, 69.8, 69.3, 65.4, 63.5, 63.2, 50.4, 47.3, 40.1, 40.1, 35.9, 33.7, 28.5, 26.3, 21.8, 21.4, 21.2, 19.6, 16.2, 14.9, 13.9, 13.8, 10.9.; HRMS (ESI (+)) calcd for C$_{42}$H$_{62}$N$_3$O$_{10}$: 768.4430. Found: 768.4432.

EXAMPLE 9 compound of formula (II): R$^1$ is (quinolin-3-yl)CH=CHCH$_2$; R$^2$ is hydrogen; R$^3$ is hydrogen; R$^4$ and R$^5$ are —C(O)—; R$^p$ is hydrogen

EXAMPLE 9A compound of formula (27) in Scheme 11: R$^1$ is CH$_2$=CHCH$_2$; R$^2$ is hydrogen; R$^3$ is C(CH$_3$)$_3$OC(O); R$^p$ is CH$_3$C(O)

A solution of Example 7D (378 mg, 0.5 mmol) in THF (10 mL) at −60° C. was treated with 1.0 M sodium bis(trimethylsilyl)amide in THF (850 μL, 0.85 mmol), stirred for 10 minutes, treated with a solution of CDI (336 mg, 1.5 mmol) in THF (7.5 mL), warmed to room temperature over 40 minutes, quenched with saturated NH$_4$Cl, diluted with dichloromethane, washed with brine, dried (Na$_2$SO$_4$), filtered, and concentrated. The concentrate was purified by flash column chromatography on silica gel with 100:1:0.2 dichloromethane/methanol/concentrated ammonium hydroxide to provide the desired product. MS (ESI(+)) m/z 771 (M+H)$^+$; 793 (M+Na)$^+$; $^1$H NMR (CDCl$_3$) δ5.70 (m, 2H), 5.29 (d, J=7.7 Hz, 1H), 5.14 (dd, J=1.36, 17.0 Hz, 1H), 5.07 (dd, J=7.46, 10.5 Hz, 1H), 4.85 (dd, J=4.5, 7.8 Hz, 1H), 4.73 (s, 1H), 4.67 (dd, J=7.7, 10.5 Hz, 1H), 4.32(d, J=7.5 Hz, 1H), 4.21 (d, J=7.5 Hz, 1H), 3.76 (q, J=6.2 Hz, 2H), 3.49 (m, 3H), 3.08 (m, 1H), 2.61 (m, 1H), 2.18 (s, 6H), 1.96 (s, 3H), 1.48 (s, 3H), 1.38 (s, 9H), 1.30 (s, 3H), 1.26 (d, J=6.7 Hz, 3H), 1.19 (d, J=6.1 Hz, 3H), 1.11 (d, J=6.8 Hz, 3H), 1.09 (d, J=6.44 Hz, 3H), (d, J=6.78 Hz, 3H), 0.87 (t, J=7.4 Hz, 3H); $^{13}$C NMR (CDCl$_3$) δ203.8, 169.6, 168.9, 156.2, 153.6, 134.7, 118.7, 101.6, 85.9, 81.6, 79.5, 78.0, 77.3, 71.5, 69.2, 64.3, 63.5, 58.8, 51.1, 45.9, 40.6, 40.6, 36.63, 33.0, 32.3, 30.4, 28.5, 28.5, 28.5, 23.3, 21.6, 21.4, 21.3, 21.0, 14.6, 14.1, 13.7, 13.3, 10.9.

EXAMPLE 9B compound of formula (27) in Scheme 11: R$^1$ is (quinolin-3-yl)CH=CHCH$_2$; R$^2$ is hydrogen; R$^3$ is C(CH$_3$)$_3$OC(O); R$^p$ is CH$_3$C(O)

A solution of Example 9A (78.3 mg, 0.1 mmol), 3-bromoquinoline (41.6 mg, 2 mmol), tetrabutylammonium bromide (51 mg, 0.15 mmol), N,N-diisopropylethylamine (51 mg, 0.4 mmol), palladium(II) acetate (2.2 mg, 0.01 mmol), and DME (2 mL) in a sealed tube was heated to 100° C. for 24 hours, cooled to room temperature, diluted with ethyl acetate, washed with 5% Na$_2$CO$_3$ and brine, dried (MgSO$_4$), filtered, and concentrated to provide the desired product.

EXAMPLE 9C compound of formula (28) in Scheme 11: R$^1$ is (quinolin-3-yl)CH=CHCH$_2$; R$^2$ is hydrogen; R$^3$ is C(CH$_3$)$_3$OC(O); R$^p$ is hydrogen A solution of Example 9B in methanol (20 mL) at room temperature was stirred for 30 hours and concentrated to provide the desired product.

EXAMPLE 9D compound of formula (II): R$^1$ is (quinolin-3-yl)CH=CHCH$_2$; R$^2$ is hydrogen; R$^3$ is hydrogen; R$^4$ and R$^5$ together are —C(O)—; R$^p$ is hydrogen A solution of Example 9C in dichloromethane (5 mL) at room temperature was treated with trifluoroacetic acid (0.5 mL), stirred for two hours, and concentrated. The concentrate was purified by flash column chromatography on silica gel with 100:2:0.1 dichloromethane/methanol/concentrated ammonium hydroxide to provide the desired product. MS (ESI(+)) m/z 768 (M+H)$^+$; 790 (M+Na)$^+$; $^1$H NMR (CDCl$_3$) δ9.03 (d, J=2.14 Hz, 1H), 8.13 (d, J=2.04 Hz, 1H), 8.06 (dd, J=1.00, 8.14 Hz, 1H), 7.80 (dd, J=1.36, 8.14 Hz, 1H), 7.65 (ddd, J=1.36, 8.14 and 8.14 Hz, 1H), 7.51 (ddd, J=1.00, 8.14 and 8.14 Hz, 1H), 6.63 (d, J=17.27 Hz, 1H), 6.36 (dt, J=5.40, 17.27 Hz, 1H), 4.89 (dd, J=4.0, 7.5 Hz, 1H), 4.75 (s, 1H), 4.37 (d, J=10.5 Hz, 1H), 4.32 (d, J=7.12 Hz, 1H), 4.08 (m, 1H), 3.90 (m, 1H), 3.84 (q, J=6.6 Hz, 2H), 3.55 (m, 1H), 3.27 (dd, J=8.0, 2.4 Hz, 1H), 3.20 (m, 1H), 2.45 (m, 1H), 2.28 (s, 6H), 1.53 (s, 3H), 1.48 (s, 3H), 1.35 (d, J=7.5 Hz, 3H), 1.32 (d, J=6.1 Hz, 3H), 1.25 (d, J=6.0 Hz, 3H), 1.11 (d, J=6.8 Hz, 3H), 1.09 (d, J=6.44 Hz, 3H), 0.82 (t, J=7.4 Hz, 3H); $^{13}$C NMR (CDCl$_3$) δ204.0, 169.2, 153.6, 149.6, 146.4, 132.8, 129.8, 129.4, 129.4, 129.3, 128.5, 128.1, 127.9, 127.7, 104.0, 85.1, 81.9, 80.0, 79.3, 77.3, 70.3, 69.6, 65.9, 63.9, 62.1, 51.1, 46.9, 40.2, 40.2, 36.3, 33.7, 32.1, 28.2, 22.9, 21.3, 21.2, 21.1, 14.9, 14.1, 13.4, 12.6, 10.2.

EXAMPLE 10 compound of formula (II): R$^1$ is (quinolin-3-yl)CH=CHCH$_2$; R$^2$ is hydrogen; R$^3$ and R$^4$ together are —CH$_2$—; R$^5$ is hydrogen; R$^p$ is hydrogen Example 7G (742 mg, 1 mmol) and formaldehyde (37%, 0.5 mL, 6.6 mmol) in methanol (5 mL) at room temperature was stirred for three days and concentrated. The concentrate was purified by flash column chromatography on silica gel with 100:2:0.2 dichloromethane/methanol/concentrated ammonium hydroxide to provide the desired product. MS (ESI(+)) m/z 754 (M+H)$^+$; $^1$H NMR (CDCl$_3$) δ9.08 (d, J=2.38 Hz, 1H), 8.15 (d, J=2.38 Hz, 1H), 8.07 (br d, J=8.47 Hz, 1H), 7.80 (dd, J=1.02, 8.14 Hz, 1H), 7.65 (ddd, J=1.35, 8.47 and 8.47 Hz, 1H), 7.51 (ddd, J=1.36, 8.14 and 8.47 Hz, 1H), 6.69 (d, J=16.27 Hz, 1H), 6.48 (dt, J=5.40, 16.27 Hz, 1H), 5.18 (dd, J=2.27, 10.51 Hz, 1H), 4.69 (d, J=5.77 Hz, 1H), 4.34 (d, J=7.46 Hz, 1H), 4.32 (s, 2H), 4.05 (m, 2H), 3.97 (q, J=6.78 Hz, 1H), 3.60 (m, 2H), 3.41 (br s, 1H), 3.28 (dd, J=7.46, 10.17 Hz, 1H), 3.17 (m, 1H), 2.28 (s, 6H), 1.46 (d, J=7.8 Hz, 3H), 1.43 (s, 3H), 1.35 (d, J=6.78 Hz, 3H), 1.26

(d, J=6.1 Hz, 3H), 1.19 (s, 3H), 1.07 (d, J=7.12 Hz, 3H), 1.06 (d, J=7.12 Hz, 3H), 0.90 (t, J=7.47 Hz, 3H); $^{13}$C NMR (CDCl$_3$) δ205.1, 169.2, 149.5, 147.4, 132.7, 129.0, 128.9, 128.6, 128.6, 127.6, 128.2, 127.3, 126.4, 103.2, 77.7, 77.5, 76.1, 75.1, 74.0, 70.5, 69.6, 65.4, 65.3, 64.6, 63.8, 50.0, 45.9, 40.1, 40.1, 35.6, 29.7, 29.0, 26.3, 21.7, 21.3, 20.6, 15.6, 15.1, 14.3, 14.0, 13.8, 10.9.

What is claimed is:

1. A compound of formula (I)

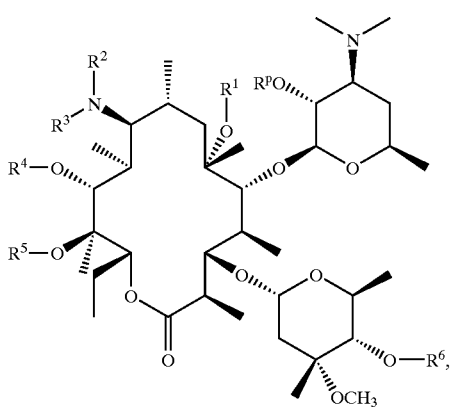

and a compound of formula (II)

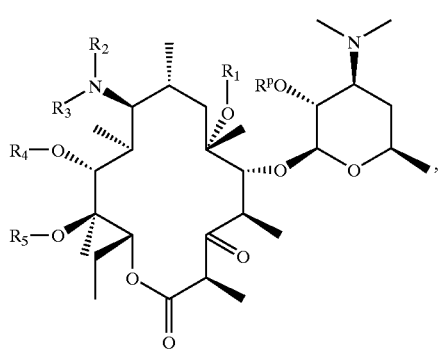

or a therapeutically acceptable salt or prodrug thereof, wherein $R^1$ is selected from the group consisting of hydrogen, alkyl, alkenyl, alkynyl, arylalkyl, arylalkenyl, arylalkynyl, (heterocycle)alkyl, (heterocycle)alkenyl, and (heterocycle)alkynyl, provided that $R^1$ is not hydrogen in compounds of formula (II);

$R^2$ and $R^3$ are independently selected from the group consisting of hydrogen, alkyl, alkenyl, alkynyl, alkanoyl, alkoxy, alkoxycarbonyl, alkylsulfonyl, arylalkyl, arylalkenyl, arylalkynyl, cycloalkyl, cycloalkylalkyl, cycloalkyloxycarbonyl, cycloalkyloyl, cycloalkylsulfonyl, cycloalkylaminocarbonyl, cycloalkylthiocarbonyl, aryl, arylalkyl, aroyl, aryloxycarbonyl, arylsulfonyl, alkylaminocarbonyl, alkylthiocarbonyl, arylaminocarbonyl, arylthiocarbonyl, heterocycle, (heterocycle)alkyl, (heterocycle)alkenyl, (heterocycle)alkynyl, (heterocycle)carbonyl, (heterocycle)aminocarbonyl, (heterocycle)oxycarbonyl, (heterocycle)thiocarbonyl, (heterocycle)sulfonyl, hydroxyl, and a nitrogen protecting group; or $R^1$ and $R^2$ together are selected from the group consisting of —C(O)—, —CH$_2$CH=CHCH$_2$—, alkylene, —CH$_2$C(O)—, and —C(O)CH$_2$—, wherein for —CH$_2$C(O)— and —C(O)CH$_2$—, each group is drawn with its left end attached to the nitrogen and its right end attached to the oxygen; or $R^2$ and $R^3$ taken together with the nitrogen atom to which they are attached form a heterocycle;

$R^4$ and $R^5$ are hydrogen; or $R^3$ and $R^4$ together are selected from the group consisting of —C(O)—, —CH$_2$CH=CHCH$_2$—, alkylene, —CH(R$^7$)—, —(CH$_2$)$_m$C(O)—, and —C(O)(CH$_2$)$_m$—, wherein m is an integer ranging from 1 to 4, and wherein for —(C$_2$)$_m$C(O)— and —C(O)(CH$_2$)$_m$—, each group is drawn with its left end attached to the nitrogen and its right end attached to the oxygen; or $R^4$ and $R^5$ together are selected from the group consisting of —CH(R$^7$)— and —C(O)—, provided that, for compounds of formula (I), when $R^4$ and $R^5$ are hydrogen and either $R^2$ or $R^3$ is alkanoyl, $R^1$ is other than hydrogen, and for compounds of formula (I), when $R^2$, $R^3$, $R^4$, and $R^5$ are hydrogen, $R^1$ is other than hydrogen;

$R^6$ is selected from the group consisting of hydrogen, alkanoyl, alkyl, aryl, carboxamido, and (heterocycle)carbonyl;

$R^7$ is selected from the group consisting of hydrogen, alkyl, alkenyl, aryl, arylalkyl, (heterocycle)alkyl and cycloalkyl; and $R^p$ is selected from the group consisting of hydrogen, trimethylsilyl, arylalkyl, aroyl, and alkanoyl.

2. A compound according to claim 1 wherein $R^1$ is selected from the group consisting of hydrogen, alkenyl, arylalkenyl, and (heterocycle)alkenyl.

3. A compound according to claim 1 wherein $R^1$ is (heterocycle)alkenyl.

4. A compound according to claim 1 wherein $R^2$ is selected from the group consisting of hydrogen, alkanoyl, arylalkyl, (heterocycle)alkyl, a nitrogen protecting group, alkyl, and alkoxy.

5. A compound according to claim 1 wherein $R^1$ and $R^2$ together are —C(O)—.

6. A compound according to claim 1 wherein $R^3$ is hydrogen.

7. A compound according to claim 1 wherein $R^2$ and $R^3$ are hydrogen.

8. A compound according to claim 1 wherein $R^4$ and $R^5$ are hydrogen.

9. A compound according to claim 1 wherein $R^3$ and $R^4$ together are —C(O)— or alkylene.

10. A compound according to claim 1 wherein $R^4$ and $R^5$ together are —C(O)— or alkylene.

11. A compound according to claim 1 wherein $R^6$ is hydrogen or alkanoyl.

12. A compound according to claim 1 wherein $R^p$ is hydrogen or alkanoyl.

13. A method of preparing compounds of formula (I)

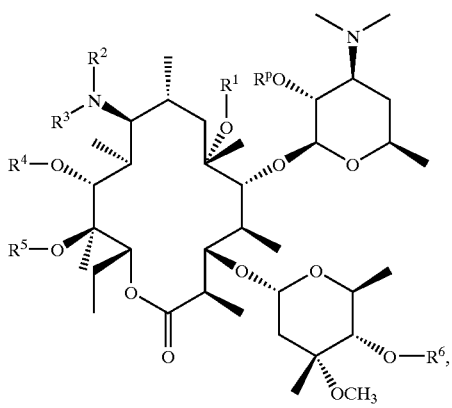

and compounds of formula (II)

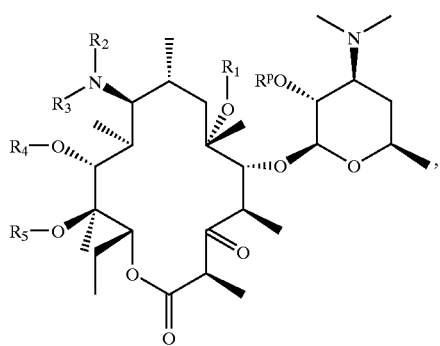

or therapeutically acceptable salts or prodrugs thereof, wherein $R^1$ is selected from the group consisting of hydrogen, alkyl, alkenyl, alkynyl, arylalkyl, arylalkenyl, arylalkynyl, (heterocycle)alkyl, (heterocycle)alkenyl, and (heterocycle)alkynyl, provided that $R^1$ is not hydrogen in compounds of formula (II);

$R^2$ and $R^3$ are independently selected from the group consisting of hydrogen, alkyl, alkenyl, alkynyl, alkanoyl, alkoxy, alkoxycarbonyl, alkylsulfonyl, arylalkyl, arylalkenyl, arylalkynyl, cycloalkyl, cycloalkylalkyl, cycloalkyloxycarbonyl, cycloalkyloyl, cycloalkylsulfonyl, cycloalkylaminocarbonyl, cycloalkylthiocarbonyl, aryl, arylalkyl, aroyl, aryloxycarbonyl, arylsulfonyl, alkylaminocarbonyl, alkylthiocarbonyl, arylaminocarbonyl, arylthiocarbonyl, heterocycle, (heterocycle)alkyl, (heterocycle)alkenyl, (heterocycle)alkynyl, (heterocycle)carbonyl, (heterocycle)aminocarbonyl, (heterocycle)oxycarbonyl, (heterocycle)thiocarbonyl, (heterocycle)sulfonyl, hydroxyl, and a nitrogen protecting group; or $R^1$ and $R^2$ together are selected from the group consisting of —C(O)—, —CH$_2$CH=CHCH$_2$—, alkylene, —CH$_2$C(O)—, and —C(O)CH$_2$—, wherein for —CH$_2$C(O)— and —C(O)CH$_2$—, each group is drawn with its left end attached to the nitrogen and its right end attached to the oxygen; or $R^2$ and $R^3$ taken together with the nitrogen atom to which they are attached form a heterocycle;

$R^4$ and $R^5$ are hydrogen; or $R^3$ and $R^4$ together are selected from the group consisting of —C(O)—, —CH$_2$CH=CHCH$_2$—, alkylene, —CH($R^7$)—, —(CH$_2$)$_m$C(O)—, and —C(O)(CH$_2$)$_m$—, wherein m is an integer ranging from 1 to 4, and wherein for —(CH$_2$)$_m$C(O)— and —C(O)(CH$_2$)$_m$—, each group is drawn with its left end attached to the nitrogen and its right end attached to the oxygen; or $R^4$ and $R^5$ together are selected from the group consisting of —CH($R^7$)— and —C(O)—;

$R^6$ is selected from the group consisting of hydrogen, alkanoyl, alkyl, aryl, carboxamido, and (heterocycle)carbonyl;

$R^7$ is selected from the group consisting of hydrogen, alkyl, alkenyl, aryl, arylalkyl, (heterocycle)alkyl and cycloalkyl; and $R^p$ is selected from the group consisting of hydrogen, trimethylsilyl, arylalkyl, aroyl, and alkanoyl; the method comprising:

(a) treating a compound of formula (Ia)

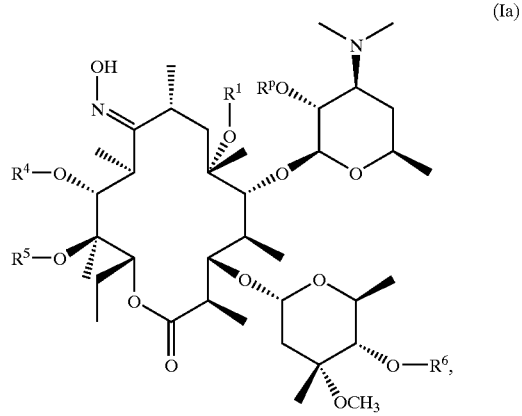

or a compound of formula (IIa)

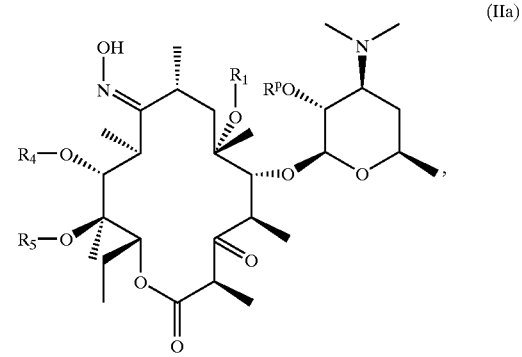

wherein, for compounds of formula (Ia) and (IIa), $R^1$, $R^4$, $R^5$, $R^6$, and $R^p$ are defined hereinabove, with a reducing agent in the presence of a first acid;

(b) optionally treating the product of step (a) with a second acid; and (c) optionally oxidizing and deprotecting the product of step (b).

14. The method of claim 13, wherein the reducing agent is selected from the group consisting of sodium cyanoborohydride, titanium(III) chloride-sodium cyanoborohydride, sodium borohydride, lithium aluminum hydride, diborane, borane complexes, hydrogen and platinum catlyst, hydrogen and palladium catalyst, and hydrogen and Raney® nickel.

15. The method of claim 13, wherein the reducing agent is titanium(III) chloride-sodium cyanoborohydride.

16. The method of claim 13, wherein the first acid is selected from the group consisting of ammonium acetate, ammonium chloride, ammonium nitrate, potassium hydrogensulfate, potassium hydrogenphosphate, potassium dihydrogenphosphate, sodium hydrogensulfate, sodium hydrogenphosphate, and sodium dihydrogenphosphate, hydrochloric acid, acetic acid, and trifluoroacetic acid.

17. The method of claim 13, wherein the first acid is ammonium acetate.

18. The method of claim 13, wherein the second acid is hydrochloric acid.

19. A method of treating bacterial infections in a mammal comprising administering to the mammal in recognized need of such treatment a therapeutically effective amount of a compound of claim 1, or a therapeutically acceptable salt or prodrug thereof.

20. A pharmaceutical composition comprising a compound of claim 1, or a therapeutically acceptable salt or prodrug thereof, and a therapeutically acceptable carrier.

21. A compound selected from the group consisting of compound of formula (I): $R^1$ is $CH_2CH=CH_2$; $R^2$ is hydrogen; $R^3$ is hydrogen; $R^4$ is hydrogen; $R^5$ is hydrogen; $R^6$ is hydrogen; $R^p$'s hydrogen;

compound of formula (I): $R^1$ is hydrogen; $R^2$ is hydrogen; $R^3$ is hydrogen; $R^4$ and $R^5$ together are —C(O)—; $R^6$ is hydrogen; $R^p$ is hydrogen;

compound of formula (I): $R^1$ and $R^2$ together are —C(O)—; $R^3$ is hydrogen; $R^4$ and $R^5$ together are —C(O)—; and $R^6$ is C(O)CH$_3$; $R^p$ is hydrogen;

compound of formula (I): $R^1$ is hydrogen; $R^2$ is $C_6H_5CH_2CH_2CH_2$; $R^3$ is hydrogen; $R^4$ and $R^5$ together are —C(O)—; $R^6$ is hydrogen; $R^p$ is hydrogen;

compound of formula (I): $R^1$ is (quinolin-3-yl)CH=CHCH$_2$; $R^2$ is C(CH$_3$)$_3$OC(O); $R^3$ is hydrogen; $R^4$ is hydrogen; $R^5$ is hydrogen; $R^6$ is C(O)CH$_3$; $R^p$ is hydrogen;

compound of formula (II): $R^1$ is (quinolin-3-yl)CH=CHCH$_2$; $R^2$ is methoxy; $R^3$ is hydrogen; $R^4$ is hydrogen; $R^5$ is hydrogen; $R^p$ is hydrogen;

compound of formula (II): $R^1$ is (quinolin-3-yl)CH=CHCH$_2$; $R^2$ is hydrogen; $R^3$ is hydrogen; $R^4$ is hydrogen; $R^5$ is hydrogen; $R^p$ is hydrogen;

compound of formula (II): $R^1$ is (quinolin-3-yl)CH=CHCH$_2$; $R^2$ is hydrogen; $R^3$ and $R^4$ together are —C(O)—; $R^5$ is hydrogen; $R^p$ is hydrogen;

compound of formula (II): $R^1$ is (quinolin-3-yl)CH=CHCH$_2$; $R^2$ is hydrogen; $R^3$ is hydrogen; $R^4$ and $R^5$ are —C(O)—; $R^p$ is hydrogen; and compound of formula (II): $R^1$ is (quinolin-3-yl)CH=CHCH$_2$; $R^2$ is hydrogen; $R^3$ and $R^4$ together are —CH$_2$—; $R^5$ is hydrogen; $R^p$ is hydrogen.

* * * * *

UNITED STATES PATENT AND TRADEMARK OFFICE
CERTIFICATE OF CORRECTION

PATENT NO.     : 6,667,338 B2   Page 1 of 1
DATED          : December 23, 2003
INVENTOR(S)    : Zhenkun Ma et al.

It is certified that error appears in the above-identified patent and that said Letters Patent is hereby corrected as shown below:

<u>Title page,</u>
Item [74], *Attorney, Agent, or Firm*, replace "Coregory" with -- Gregory --.

Signed and Sealed this

Eleventh Day of April, 2006

JON W. DUDAS
*Director of the United States Patent and Trademark Office*